(12) United States Patent
Takeda et al.

(10) Patent No.: US 10,302,610 B2
(45) Date of Patent: May 28, 2019

(54) GENERATION SOURCE ANALYZING DEVICE AND GENERATION SOURCE ANALYZING METHOD

(71) Applicant: FUJI ELECTRIC CO., LTD., Kanagawa (JP)

(72) Inventors: Naoki Takeda, Yokohama (JP); Yoshiki Hasegawa, Hino (JP); Kazuhiro Koizumi, Sagamihara (JP); Bo Li, Hachioji (JP)

(73) Assignee: FUJI ELECTRIC CO., LTD., Kanagawa (JP)

( * ) Notice: Subject to any disclaimer, the term of this patent is extended or adjusted under 35 U.S.C. 154(b) by 215 days.

(21) Appl. No.: 15/494,543

(22) Filed: Apr. 24, 2017

(65) Prior Publication Data
US 2017/0315105 A1    Nov. 2, 2017

(30) Foreign Application Priority Data
Apr. 28, 2016    (JP) ................. 2016-092075

(51) Int. Cl.
*G01N 33/00* (2006.01)
*G01N 15/06* (2006.01)
(Continued)

(52) U.S. Cl.
CPC ..... *G01N 33/0036* (2013.01); *G01N 33/0042* (2013.01); *G01N 1/2202* (2013.01);
(Continued)

(58) Field of Classification Search
CPC .......... G01N 33/0036; G01N 33/0042; G01N 1/2202; G01N 2001/2223; G01N 2015/0046
See application file for complete search history.

(56) References Cited

U.S. PATENT DOCUMENTS

2011/0032516 A1* 2/2011 Zhou ............... G01N 21/39
356/73
2013/0011930 A1* 1/2013 Takegawa ........... G01N 1/2202
436/173

FOREIGN PATENT DOCUMENTS

JP    2003-255055 A    9/2003

OTHER PUBLICATIONS

Tokyo Metropolitan Government Particulate Matter Investigative Commission-Simulation Working Report, the seventh Particulate Matter Investigative Commission, Jul. 20, 2011, Tokyo Metropolitan Government Particulate Matter Investigative Commission Report Collection.

(Continued)

*Primary Examiner* — Jennifer Wecker

(57) ABSTRACT

To analyze a generation source of a target component emitted in a form of a gas. To provide a generation source analyzing device comprising an acquiring section which acquires a concentration measurement value of a gas which includes a target component, and a concentration measurement value of a particle component which is generated in association with the gas, and an analyzing section which analyzes a distance from a measurement point to a generation source of the target component based on a concentration measurement value of the gas and a concentration measurement value of the particle component. The acquiring section may acquire a concentration measurement value of a precursor gas which becomes a raw material which generates the particle component, and a concentration measurement value of a secondary generated particle component which is generated from the precursor gas.

18 Claims, 19 Drawing Sheets

(51) Int. Cl.
  *G01N 1/22* (2006.01)
  *G01W 1/00* (2006.01)
  *G01N 15/00* (2006.01)
(52) U.S. Cl.
  CPC ............... *G01N 2001/2223* (2013.01); *G01N 2015/0046* (2013.01)

(56) References Cited

OTHER PUBLICATIONS

Tokyo Metropolitan Government Particulate Matter Investigative Commission—Receptor Working Report, the seventh Particulate Matter Investigative Commission, Jul. 20, 2011, Tokyo Metropolitan Government Particulate Matter Investigative Commission Report Collection.

Ueno Hiroyuki,"Current situation of PM 2.5 environment in Tokyo and situation of generation source survey", Symposium —Current situation of particulate matter (PM 2.5) and future tasks (Abstracts), Oct. 22, 2010, held by Bureau of Environment Tokyo Metropolitan Government, Ministry of the Environment Government of Japan, Japan Society for Atmospheric Environment.

Hayami Hiroshi et al."Air pollution flowing from the western end of Japan",Oct. 31, 2004, the twelfth Sanitary Engineering Symposium Report Collection.

Hiromasa Ueda,"Behavior of Atmospheric Aerosol During the Long-Range Transport of Air Pollution", Aerosol Research vol. 3(1988) No. 3 Autumn p. 178-p. 186, Japan Association of Aerosol Science and Technology.

\* cited by examiner

GENERATION SOURCE ANALYZING DEVICE AND GENERATION SOURCE ANALYZING METHOD

The contents of the following Japanese patent application are incorporated herein by reference:
NO. 2016-092075 filed in JP on Apr. 28, 2016.

BACKGROUND

Technical Field

The present invention relates to a generation source analyzing device and a generation source analyzing method.

Conventionally, a method for analyzing a generation source of a particulate matter such as PM 2.5 by a simulation model is known (Patent Document 1, Non-Patent Document 1). Also, as a method for analyzing a generation source based on a measurement value of a particle component concentration at a measurement point apart from a generation source, an analyzing method using a receptor model is known (Non-Patent Document 2). As analyzing methods using a receptor model, a CMB method (Chemical Mass Balance method) using a measurement value at a measurement point and generation source information and a PMF method (Positive Matrix Factorization method) using a plurality of measurement values are known.

Regarding a measuring technology, an apparatus which quantitatively measures a component of a particulate matter is known (Patent Document 2). The particulate matter which is subject to measurement includes a primary particle component and a secondary generated particle component. The primary particle component is emitted as a particle directly from a generation source. The secondary generated particle component is a component in which a material emitted as a precursor gas is granulated by a chemical reaction in the atmosphere. It is reported that about 50% of the secondary generated particle component is included in the particulate matter (Non-Patent Document 3). It is reported that the precursor gas and the secondary generated particle component dwell in the atmosphere (Non-Patent Document 4 and Non-Patent Document 5).

PRIOR ART DOCUMENTS

Patent Documents

Patent Document 1: Japanese Patent Application Publication No. 2003-255055
Patent Document 2: WO No. 2011/114587

Non-Patent Documents

Non-Patent Document 1: Tokyo Metropolitan Government Particulate Matter Investigative Commission—Simulation Working Report, the seventh Particulate Matter Investigative Commission, Jul. 20, 2011, Tokyo Metropolitan Government Particulate Matter Investigative Commission Report Collection.
Non-Patent Document 2: Tokyo Metropolitan Government Particulate Matter Investigative Commission—Receptor Working Report, the seventh Particulate Matter Investigative Commission, Jul. 20, 2011, Tokyo Metropolitan Government Particulate Matter Investigative Commission Report Collection.
Non-Patent Document 3: Ueno Hiroyuki, "Current situation of PM 2.5 environment in Tokyo and situation of generation source survey", Symposium—Current situation of particulate matter (PM 2.5) and future tasks (Abstracts), Oct. 22, 2010, held by Bureau of Environment Tokyo Metropolitan Government, Ministry of the Environment Government of Japan, Japan Society for Atmospheric Environment. Non-Patent Document 4: Hayami Hiroshi, and other two authors, "Air pollution flowing from the western end of Japan", Oct. 31, 2004, the twelfth Sanitary Engineering Symposium Report Collection. Non-Patent Document 5: Hiromasa Ueda "Behavior of Atmospheric Aerosol During the Long-Range Transport of Air Pollution", Aerosol Research Vol. 3 (1988) No. 3 Autumn p. 178-p. 186, Japan Association of Aerosol Science and Technology However, the analyzing method by the simulation model is just analyzing based on a calculated value. On the other hand, the analyzing method using the receptor model analyzes a generation source based on a measurement value of a particle component concentration. However, the receptor model is mainly used for analysis of a primary particle component. Therefore, it has been difficult to analyze a generation source of a target component which is emitted in a form of a gas from the generation source.

SUMMARY

A first aspect of the present invention provides a generation source analyzing device. The generation source analyzing device may comprise an acquiring section and an analyzing section. The acquiring section may acquire a concentration measurement value of a gas and a concentration measurement value of a particle component. The gas may include a target component. The particle component may be generated in association with the gas. The analyzing section may analyze a distance from a measurement point to a generation source of the target component based on the concentration measurement value of the gas and the concentration measurement value of the particle component.

The acquiring section may acquire a concentration measurement value of a precursor gas and a concentration measurement value of a secondary generated particle component. The precursor gas may be a raw material to generate the particle component. The secondary generated particle component may be generated from the precursor gas.

The analyzing section may estimate the distance to at least one generation source is closer than a reference distance if the concentration measurement value of the precursor gas is higher than a predetermined value, and the concentration measurement value of the secondary generated particle component is lower than a first threshold value.

The analyzing section may estimate the distance to a generation source which is positioned the nearest is farther than a reference distance if the concentration measurement value of the secondary generated particle component is higher than a predetermined value, and the concentration measurement value of the precursor gas is lower than a second threshold value.

The acquiring section may acquire wind speed data in association with concentration measurement values of the precursor gas and the particle component. The analyzing section may have a reference distance setting section. The reference distance setting section may set the reference distance longer when a wind speed value in association with the concentration measurement value is larger.

The analyzing section may have a calculating section. The calculating section may calculate an equilibrium state concentration of the secondary generated particle component which is generatable from the precursor gas, based on the concentration measurement value of the precursor gas. The analyzing section may estimate the distance to the generation source based on the calculated equilibrium state concentration and the concentration measurement value of the secondary generated particle component.

The acquiring section may acquire the concentration measurement value for each type of a plural types of the precursor gases, and the concentration measurement values for each type of the secondary generated particle components which are generated from the respective precursor gases. The analyzing section may analyze a distance to a generation source for each type of the precursor gases.

The acquiring section may respectively acquire time-series data as concentration measurement values of a precursor gas and concentration measurement values of the particle component. The analyzing section may analyze the distance to the generation source based on a correlation value between time-series data of the concentration measurement values of the precursor gas and time-series data of the concentration measurement values of the particle component.

The analyzing section may analyze the distance to the generation source based on a correlation value between data for a first time range in time-series data of the concentration measurement values of the precursor gas, and data for a second time range in time-series data of the concentration measurement values of the particle component. The second time range may be more delayed than the first time range.

The acquiring section may acquire wind speed data in association with a concentration measurement value of the precursor gas and the particle component. The analyzing section may have a delay time setting section. The delay time setting section may set a delay time of the second time range with respect to the first time range depending on the wind speed data.

When at least one of the concentration measurement value of the particle component and the concentration measurement value of the precursor gas is larger than or equal to a predetermined lower limit value, and when the correlation value between time-series data of the concentration measurement value of the particle component and time-series data of the concentration measurement value of the precursor gas is higher than a predetermined reference, the analyzing section may estimate the distance to at least the one generation source is closer than a predetermined reference distance.

The analyzing section may have a separating section. The separating section may respectively separate time-series data of the concentration measurement value of the precursor gas and time-series data of the concentration measurement value of the particle component into a first frequency band component and a second frequency band component. The analyzing section may analyze a distance to a first generation source based on a correlation value between the first frequency band component regarding the concentration measurement value of the precursor gas and the first frequency band component regarding the concentration measurement value of the particle component. The analyzing section may analyze a distance to a second generation source based on a correlation value between the second frequency band component regarding the concentration measurement value of the precursor gas and the second frequency band component regarding the concentration measurement value of the particle component.

The acquiring section may further acquire weather data. The analyzing section may correct an analysis result regarding a distance to the generation source using the weather data.

The acquiring section may acquire wind speed data as the weather data.

The acquiring section may acquire wind direction data as the weather data. The analyzing section may have a direction analyzing section. The direction analyzing section may analyze a direction from the measurement point to the generation source of the target component based on the concentration measurement value of the gas including the target component, the concentration measurement value of the particle component which is generated in association with the gas, and the wind direction data.

The acquiring section may acquire rainfall data as the weather data. The analyzing section may output that an analysis of the distance to the generation source is difficult when rainfall is observed in an area on a route from the measurement point to the generation source.

The acquiring section may acquire concentration measurement values of a precursor gas at a plurality of measurement points and concentration measurement values of the particle component at a plurality of measurement points. The analyzing section may analyze the distance to the generation source based on the concentration measurement values of the precursor gas at a plurality of measurement points and the concentration measurement values of the particle component at a plurality of measurement points.

A second aspect of the present invention provides a generation source analyzing method. The generation source analyzing method may comprise acquiring a concentration measurement value of a gas and a concentration measurement value of a particle component.

The gas may include a target component. The particle component may be generated in association with the gas. The generation source analyzing method may comprise analyzing a distance from a measurement point to a generation source of a target component based on a concentration measurement value of the gas and a concentration measurement value of the particle component.

The summary clause does not necessarily describe all necessary features of the embodiments of the present invention. The present invention may also be a sub-combination of the features described above.

DESCRIPTION OF EXEMPLARY EMBODIMENTS

Hereinafter, the present invention is described through the embodiments of the invention. However, the following embodiments do not limit the invention according to the scope of claim. Also, all the combinations of the features described in the embodiments are not necessarily essential to means provided by aspects of the invention.

Figure 1:
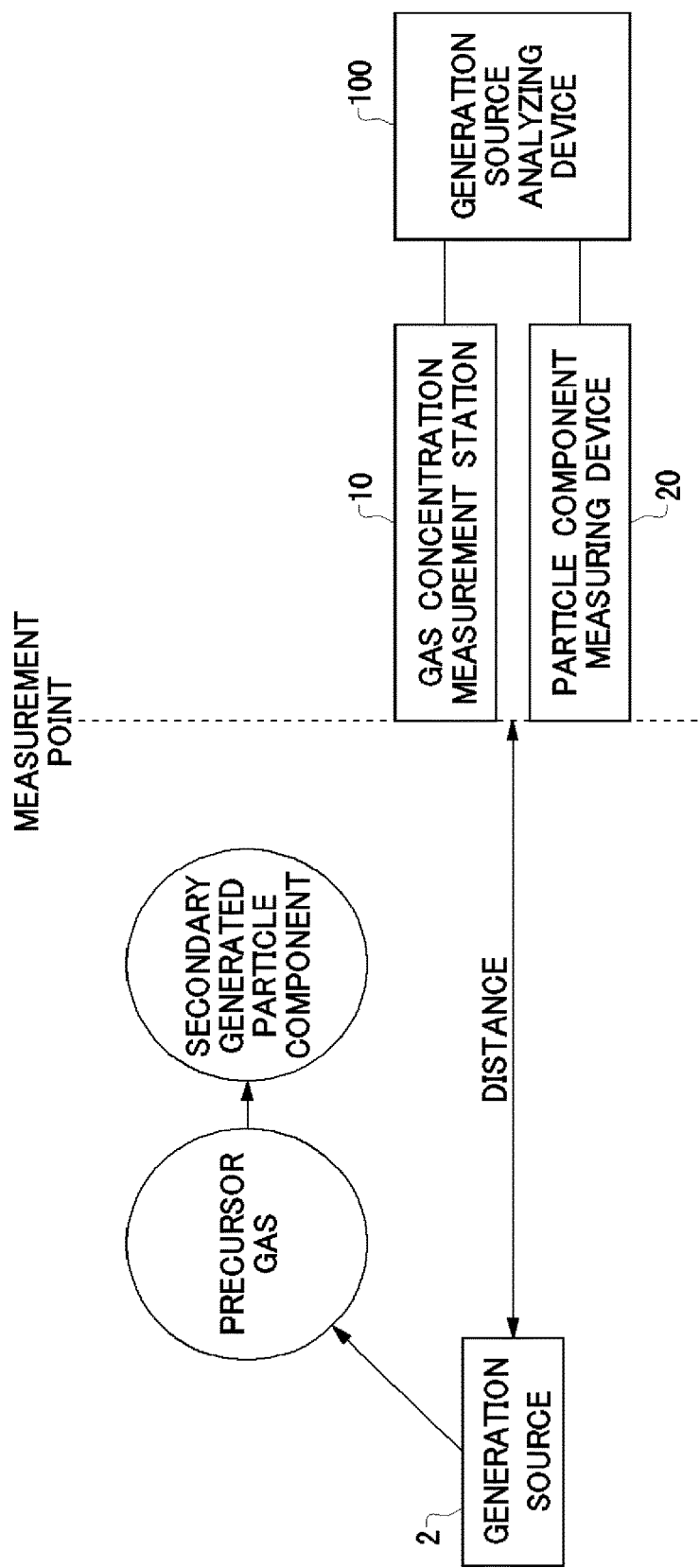
FIG. 1 is a diagram describing an overview of a generation source analyzing device of the first embodiment.

FIG. 1 is a diagram describing an overview of a generation source analyzing device 100 of the embodiment of the present invention. The generation source analyzing device 100 acquires a concentration measurement value of a gas which includes a target component, and a concentration measurement value of a particle component which is generated in association with the gas. The gas may be a precursor gas which is a raw material to generate a particle component. The particle component may be a secondary generated particle component generated from the precursor gas.

In the present example, the generation source analyzing device 100 is communicatively connected to a gas concentration measurement station 10 and a particle component measuring device 20 at a measurement point. The generation source analyzing device 100 may acquire a concentration measurement value of a precursor gas from the gas concentration measurement station 10. The generation source analyzing device 100 may acquire a concentration measurement value of the secondary generated particle component from the particle component measuring device 20.

The generation source analyzing device 100 analyzes a distance from a measurement point to a generation source 2 of the target component which is included in the gas based on a concentration measurement value of the gas and a concentration measurement value of the particle component at the measurement point. In the specification, analyzing a distance to the generation source 2 includes estimating a distance to the generation source 2. Estimating the distance may include determining whether the generation source 2 be in a distance range farther than a predetermined distance.

In order to analyze the distance, difference of a residence time between the gas and the particle is used. It is preferable that a gas concentration and a particle component concentration is measured at the same point. However, a measurement point of a gas concentration and a measurement point of a particle component concentration may be apart by a distance which is negligible compared to a distance between the generation source 2 and the measurement point of the gas concentration, and a distance between the generation source 2 and the measurement point of the particle component concentration.

A secondary generated particle in the atmosphere includes mainly ammonium sulfates (sulfates), ammonium nitrates (nitrates), and secondary organic aerosols (SOA). Sulfur dioxides ($SO_2$) are present as a precursor gas of ammonium sulfates. Nitrogen oxides ($NO_X$) are present as a precursor gas of ammonium nitrates.

A secondary generated particle such as ammonium sulfates and ammonium nitrates is emitted in a form of a gas such as $SO_2$, $NO_X$ from the generation source 2. These precursor gases change into particles such as ammonium sulfates and ammonium nitrates by chemical reacting in the atmosphere. Not all precursor gases in the atmosphere are granulated.

According to the above-mentioned Non-Patent Documents 4 and 5, a residence time of a precursor gas in the atmosphere is about three days at the longest, and a moving distance of the precursor gas is 100 kilometers order. On the other hand, a residence time of granulated secondary generated particles in the atmosphere reaches two-fold to three-fold of a residence time of the precursor gas, and a moving distance of the secondary generated particle is 1,000 kilometers order.

Figure 2:
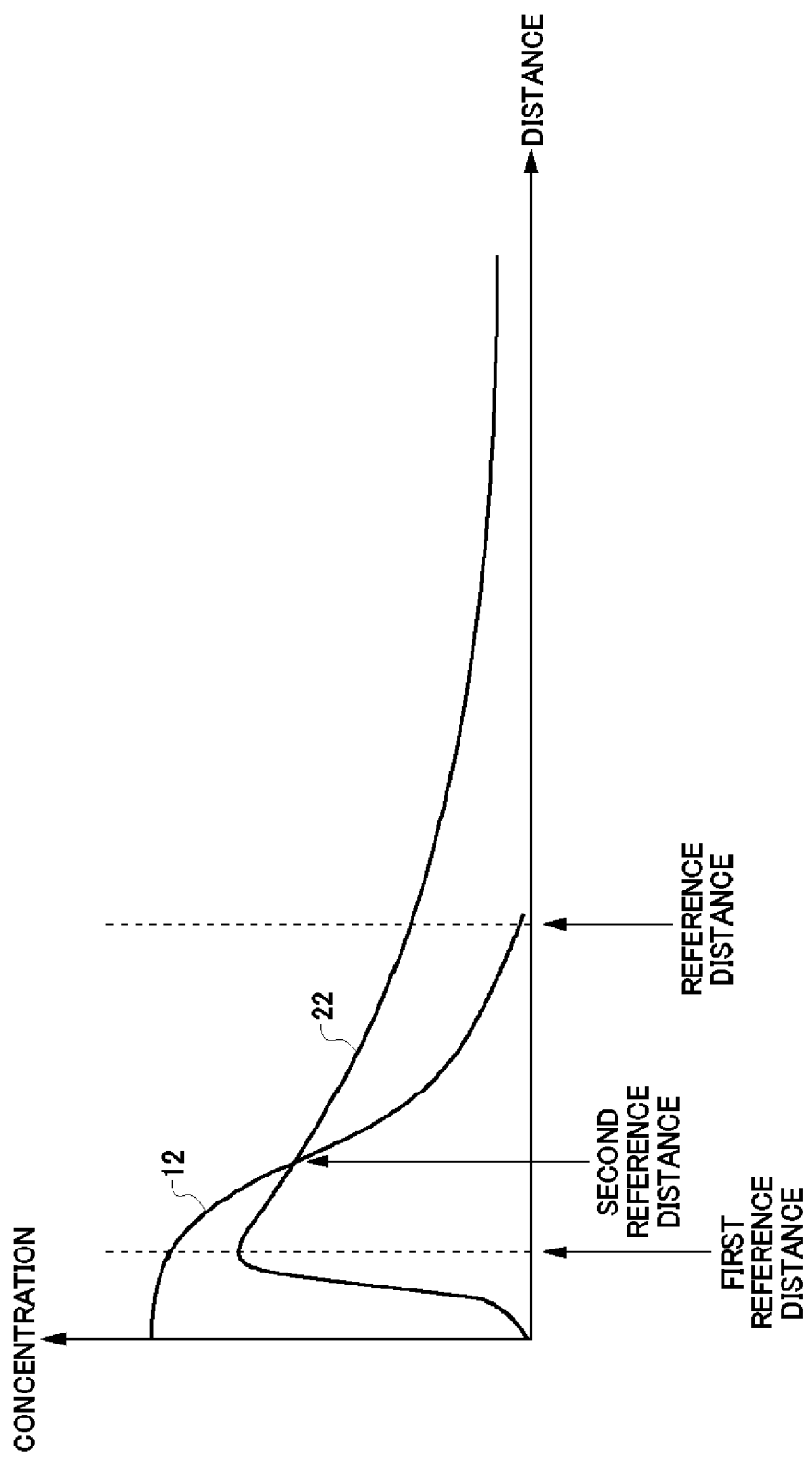
FIG. 2 is a diagram showing one example of a diffusion distribution depending on a distance from a generation source 2, regarding a precursor gas concentration 12 and a secondary generated particle component concentration 22.

FIG. 2 is a diagram showing one example of a diffusion distribution depending on a distance from a generation source 2, regarding a precursor gas concentration 12 and a secondary generated particle component concentration 22. In FIG. 2, units of a precursor gas concentration 12 and a secondary generated particle component concentration 22 are aligned. For instance, when a gas concentration measurement station 10 measures a precursor gas concentration 12 in a volume concentration, and a particle component measuring device 20 measures a secondary generated particle component concentration 22 in a mass concentration, the generation source analyzing device 100 converts these concentrations into a unified unit such as a molar concentration. If a diffusion in the air is sufficient, there is ideally no secondary generated particles at a point of the generation source 2. As being apart from the generation source 2, a secondary generated particle is gradually generated by a chemical reaction. At a point apart from the generation source 2 by several hundred kilometers which is a diffusion range of the precursor gas (diffusion limit point), the precursor gas concentration 12 shows a value around zero, ideally, only the secondary generated particle is present.

Therefore, by comparing the precursor gas concentration 12 and the secondary generated particle component concentration 22, the distance from the measurement point to the generation source 2 can be estimated. As shown in FIG. 2, in a local area of the generation source 2, the precursor gas concentration 12 is higher compared to the secondary generated particle component concentration 22. And, if the distance from the generation source 2 exceeds a predetermined distance, the secondary generated particle component concentration 22 becomes higher compared to the precursor gas concentration 12. In a wide area which is far from the generation source 2, the secondary generated particle component concentration 22 is higher compared to the precursor gas concentration 12. Also, in an area located at the distance which is larger than or equal to a movable distance of the precursor gas, and smaller than or equal to a movable distance of the secondary generated particle, the precursor gas concentration 12 becomes almost zero, but the secondary generated particle component concentration 22 does not become zero.

In an example shown in FIG. 2, a movable distance of a precursor gas is set as a reference distance. If the precursor gas concentration 12 is almost zero, while the secondary generated particle component concentration 22 is larger than or equal to the predetermined value, the generation source analyzing device 100 may determine that the distance from the generation source 2 to the measurement point is larger than or equal to the reference distance (that is, a wide area). Also, the generation source analyzing device 100 may determine that the distance from the generation source 2 to the measurement point is smaller than or equal to the reference distance (that is, local area) when the precursor gas concentration 12 and the secondary generated particle component concentration 22 are respectively larger than or equal to the predetermined value.

Also, a distance corresponding to an intersection point of a distance distribution curve of the precursor gas concentration 12 and a distance distribution curve of the secondary generated particle component concentration 22 may be set as a second reference distance. Also, an area in which a distance from the generation source 2 is within the first reference distance may be set as a local area. An area in which a distance from the generation source 2 is larger than or equal to the second reference distance may be set as a wide area. The first reference distance is set as a distance shorter than the above second reference distance. The first reference distance, for instance, corresponds to a distance which is about larger than or equal to 1 km, and smaller than or equal to 50 km, and a ratio of the precursor gas concentration 12 and the secondary generated particle component concentration 22 corresponding to the first reference distance is determined in advance by measurement and the like.

Figure 3:
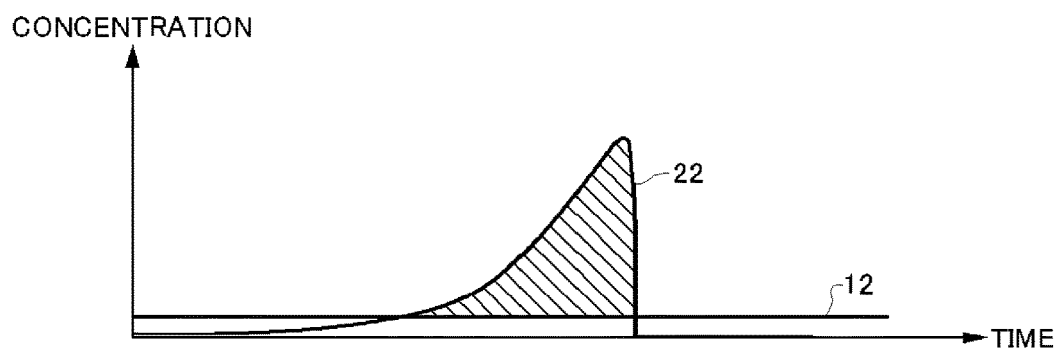
FIG. 3 is a diagram showing one example of a variation over time of a precursor gas concentration 12 and a secondary generated particle component concentration 22 in a wide area.

FIG. 3 is a diagram showing one example of a variation over time of a precursor gas concentration 12 and a secondary generated particle component concentration 22 in a wide area. In FIG. 3, a case in which an emission of a precursor gas in a generation source 2 peaks at an initial time is shown. Although the precursor gas is emitted in the generation source 2, a precursor gas concentration 12 in a wide area shows a value around zero. On the other hand, a secondary generated particle can fly beyond a diffusion range of the precursor gas. Therefore, a secondary generated particle component concentration 22 increases or decreases depending on an increase or decrease of an amount of a precursor gas emitted from the generation source 2. Also, an increase or decrease of a secondary generated particle component concentration 22 in a wide area is delayed depending on a diffusion speed of a secondary generated particle and the like with respect to an increase or decrease of an amount of a precursor gas emitted in the generation source 2.

Figure 4:
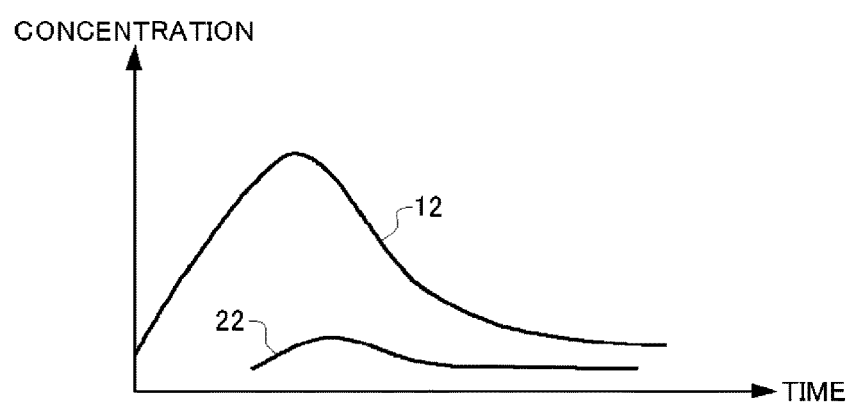
FIG. 4 is a diagram showing one example of a variation over time of a precursor gas concentration 12 and a secondary generated particle component concentration 22 within a diffusion range of a precursor gas.

FIG. 4 is a diagram showing one example of a variation over time of a precursor gas concentration 12 and a secondary generated particle component concentration 22 in a local area. FIG. 4 shows a variation over time of a concentration at a point within a diffusion range of a precursor gas from a generation source 2. Near the generation source 2, the precursor gas is diffused before the precursor gas changes into a secondary generated particle. Therefore, near the generation source 2, a secondary generated particle component concentration 22 shows a lower value compared to a precursor gas concentration 12.

As above, there are a number of methods in order to estimate a distance to the generation source 2 using difference of a residence time between the precursor gas and the particle. As mentioned above, when the secondary generated particle component concentration 22 is almost zero (for instance, smaller than or equal to the first threshold value), while the precursor gas concentration 12 is larger than or equal to the predetermined value, it can be estimated that the distance to the generation source 2 is closer. As mentioned above, when the precursor gas concentration 12 is almost zero (for instance, smaller than or equal to the second threshold value), while the secondary generated particle component concentration 22 is larger than or equal to the predetermined value, it can be estimated that the distance to the generation source 2 is farther than the movable distance of the precursor gas.

Also, an attenuation of the precursor gas concentration 12 with respect to the distance from the generation source 2 is sharper than an attenuation of the secondary generated particle component concentration 22 with respect to the distance from the generation source 2. For this reason, depending on the distance from the generation source 2, a magnitude relation, a ratio, a difference and the like of the precursor gas concentration 12 and the secondary generated particle component concentration 22 change. The generation source analyzing device 100 can estimate the distance to the generation source 2 based on the magnitude comparison of the precursor gas concentration 12 and the secondary generated particle component concentration 22, a ratio of the precursor gas concentration 12 and the secondary generated particle component concentration 22, or difference of the precursor gas concentration 12 and the secondary generated particle component concentration 22.

Also, as another analyzing method, there is a method for respectively acquiring time-series data of concentration measurement values of a precursor gas and time-series data of concentration measurement values of a secondary generated particle component, and analyzing a distance to a generation source 2 based on a correlation value between time-series data of a measurement value of a precursor gas concentration 12 and time-series data of a measurement value of a secondary generated particle component concentration 22. In an area in which the precursor gas and the secondary generated particle are both observed, the distance to the generation source 2 can be analyzed.

Figure 5:
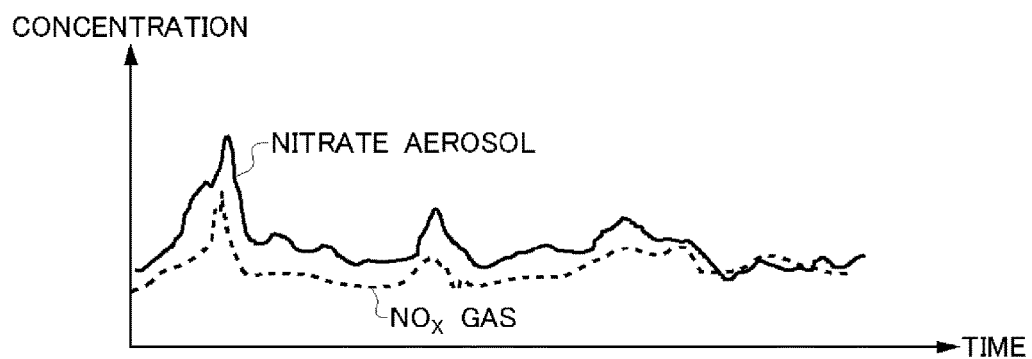
FIG. 5 is a diagram showing one example of a correlation between a precursor gas concentration 12 and a secondary generated particle component concentration 22 within a diffusion range of a precursor gas.

FIG. 5 is a diagram showing one example of a relationship between a precursor gas concentration 12 and a secondary generated particle component concentration 22 within a diffusion range of a precursor gas.

Figure 6:
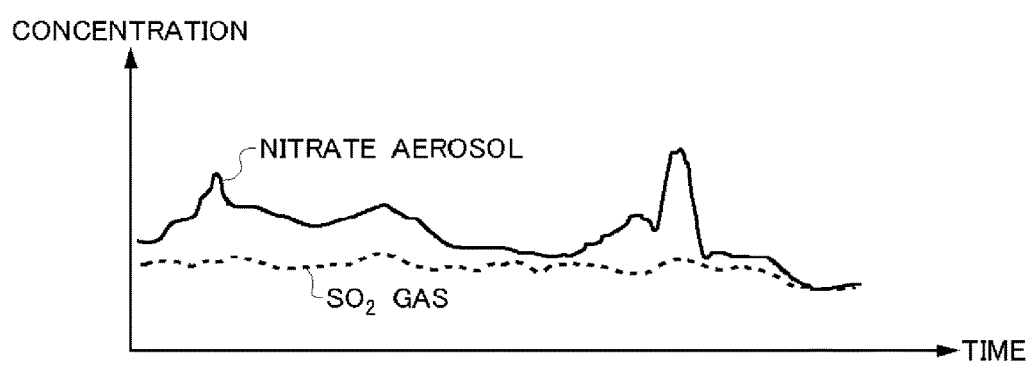
FIG. 6 is a diagram showing one example of a non-correlation between a precursor gas concentration 12 and a secondary generated particle component concentration 22 within a diffusion range of a precursor gas.

FIG. 6 is a diagram showing one example of a relationship between a precursor gas concentration 12 and a secondary generated particle component concentration 22 outside a diffusion range of a precursor gas. When the generation source 2 is relatively at a short distance, the precursor gas concentration 12 and the secondary generated particle component concentration 22 change depending on a variation of an emitting force of a precursor gas in the generation source 2. For this reason, the precursor gas concentration 12 and the secondary generated particle component concentration 22 are in correlation.

Specifically, as shown in FIG. 5, when the generation source 2 is within a diffusion range of the precursor gas, the precursor gas concentration 12 and the secondary generated particle component concentration 22 are in correlation. FIG. 5 shows a case in which the precursor gas is a $NO_X$ gas, and the particle component is a nitrate aerosol. However, if the precursor gas is a $SO_2$ gas and the particle component is a sulfate aerosol, in the case the generation source 2 is within a diffusion range of the precursor gas, a same correlation appears.

On the other hand, as shown in FIG. 6, when a distance to the generation source 2 is farther than a diffusion range of the precursor gas, because the precursor gas concentration 12 is approximately a constant value, the precursor gas concentration 12 and the secondary generated particle component concentration 22 are not in correlation. FIG. 6 shows a case in which the precursor gas is a $SO_2$ gas, and the particle component is a sulfate aerosol. However, if the precursor gas is a $NO_X$ gas and the particle component is a sulfate aerosol, in the case the generation source 2 is farther than a diffusion range of the precursor gas, there is no correlation.

In a process in which the particle is generated from the precursor gas, an average speed of conversion from a NOx to an ammonium nitrate is 14.7%/h, and an average speed of conversion from a $SO_2$ to an ammonium sulfate is 3.7%/h (Non-Patent Document 5). Therefore, materials which are granulated relatively soon such as ammonium nitrates sometimes need time about larger than or equal to an hour, and smaller than or equal to 10 hours to be granulated. Ammonium sulfates sometimes need time about larger than or equal to an hour, and smaller than or equal to 50 hours to be granulated. Therefore, although a concentration of the precursor gas changes, a concentration of the secondary generated particle does not change immediately but a concentration of the secondary generated particle sometimes changes while being delayed for a predetermined time.

Figure 7:
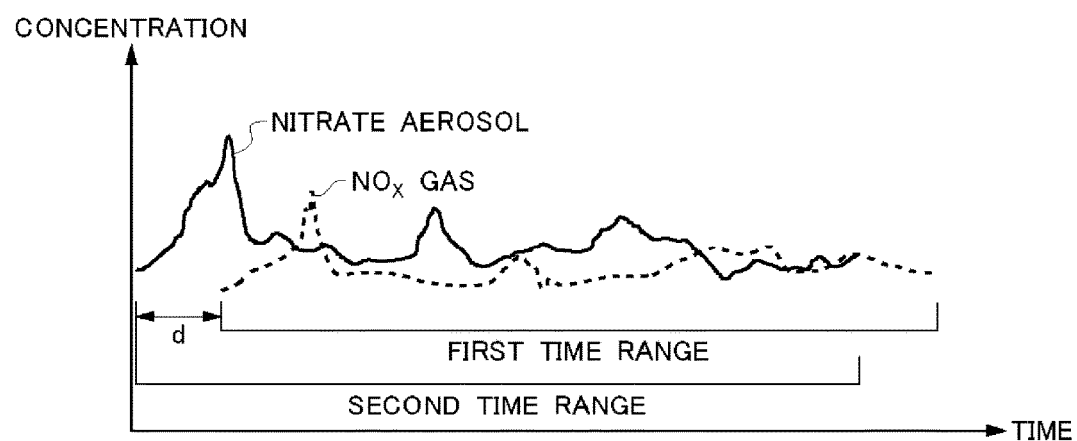
FIG. 7 is a diagram showing one example of a delay time between a variation over time of a precursor gas concentration 12 and a variation over time of a secondary generated particle component concentration 22.

FIG. 7 is a diagram showing one example of a delay time between a variation over time of a precursor gas concentration 12 and a variation over time of a secondary generated particle component concentration 22. As shown in FIG. 7, the generation source analyzing device 100 may analyze a distance to the generation source 2 based on a correlation value between data of a first time range in time-series data of a concentration measurement value of a precursor gas and a data of a second time range in time-series data of a concentration measurement value of the secondary generated particle component. The second time range is more delayed than the first time range by a delay time d.

Figure 8:
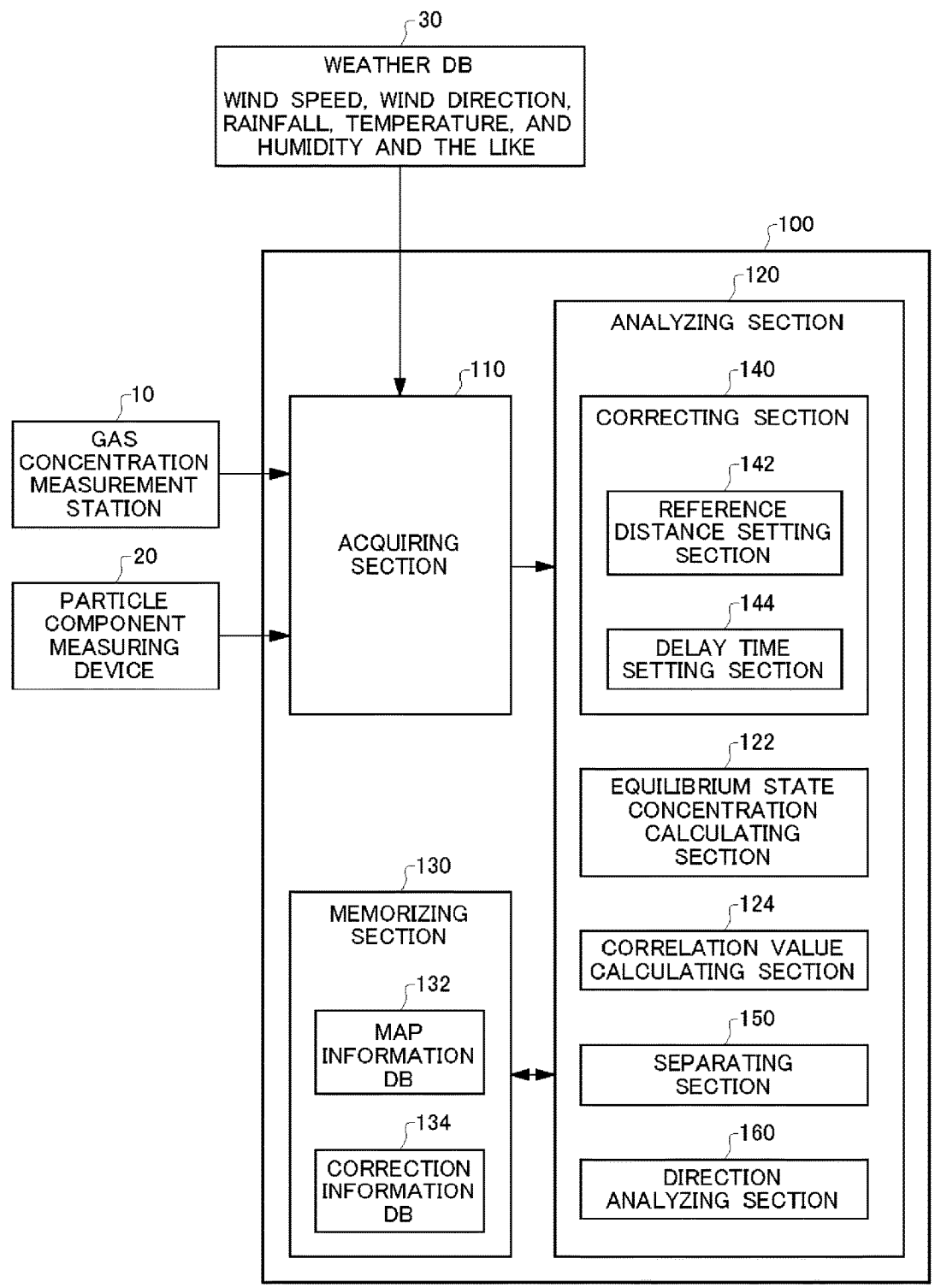
FIG. 8 is a diagram showing a configuration of a generation source analyzing device 100 of the embodiment of the present invention.

FIG. 8 is a diagram showing a configuration of a generation source analyzing device 100 of the embodiment. The generation source analyzing device 100 comprises an acquiring section 110 and an analyzing section 120. Also, the generation source analyzing device 100 may comprise a memorizing section 130. The memorizing section 130 may have various database such as a map information DB 132 and a correction information DB 134 (hereinafter, 'database' is written as 'DB'). The acquiring section 110 acquires a concentration measurement value of a gas, and a concentration measurement value of a particle component which is generated in association with the gas. In the present invention, 'a particle component which is generated in association with a gas' may include not only a secondary generated particle component, but also a primary particle component which is emitted together with the gas in the generation source 2, such as a black carbon. In the generation source 2, an emission amount of a primary particle component such as a black carbon varies similarly as an emission amount of a gas.

For instance, if a $NO_X$ gas increases due to vehicle emission gas around the measurement point, and a nitrate aerosol is generated, due to the vehicle emission, a tendency that a primary particle such as black carbon increases is sometimes shown. In this case, a concentration of a primary particle component such as black carbon and a concentration of a secondary generated particle have a correlation.

Therefore, when comparing a concentration measurement value of the precursor gas and a concentration of a primary particle such as black carbon, the precursor gas is zero at a measurement point apart from the generation source 2 exceeding a diffusion range of the precursor gas, ideally, a concentration of the primary particle is observed. Also, at a measurement point within a diffusion range of the precursor gas from the generation source 2, time-series data of a measurement value of the precursor gas concentration 12 and time-series data of a measurement value of a primary particle concentration sometimes show a correlation. In this case, the primary particle component can be analyzed as a particle component which is generated in association with the gas. However, in the following description, a case in which 'a particle component which is generated in association with the gas' is a secondary generated particle component is described as an example.

The acquiring section 110, as shown in FIG. 5 and FIG. 6, may acquire a concentration measurement value for each type of a plural types of the precursor gas such as nitrogen oxides ($NO_X$) and sulfur dioxides ($SO_2$). Also, the acquiring section 110 may acquire a concentration measurement value for each type of a plural types of secondary generated particle components such as ammonium sulfates (sulfate) and ammonium nitrates (nitrate) which are generated from respective precursor gases.

In the present example, the acquiring section 110 acquires a concentration measurement value of a gas from the gas concentration measurement station 10. The gas concentration measurement station 10 may be a measuring equipment which is managed by municipalities and the like, or may be an individual gas concentration measuring apparatus. A concentration of nitrogen oxides ($NO_X$) may be measured by the chemiluminescence method or the Salzman method, and a concentration of sulfur dioxides (SO$_2$) may be measured by the ultraviolet fluorescence method or the conductometric method.

In the present example, the acquiring section 110 acquires a concentration measurement value of a particle component from the particle component measuring device 20. For analysis of the generation source 2, comparison of an absolute amount of the precursor gas and an absolute amount of a concentration of the particle component is needed. Therefore, it is preferable that the particle component measuring device 20 be a measuring apparatus which can quantify the absolute amount of the concentration of the particle component. Also, it is preferable that the particle component measuring device 20 have less variation than an allowable value regarding a detection efficiency when measuring a particle as well. For instance, the particle component measuring device 20 is an apparatus which can perform quantitative analysis accurately, by capturing a particle by a mesh-shaped particle trap, through irradiation of the mesh-shaped particle trap with a particle beam, yielding a desorbed component of the particle through irradiation of the caught particle with an energy beam, and performing mass analysis on the desorbed component (Patent Document 2). However, a measurement method of a gas concentration and a measurement method of a particle component concentration are not limited.

The generation source analyzing device 100 and the particle component measuring device 20 may be configured as separate apparatuses being accommodated in separate cases. The particle component measuring device 20 and the generation source analyzing device 100 may also be accommodated in a single case. The particle component measuring device 20 itself may have a function as the generation source analyzing device 100. This eliminates a burden to arrange another generation source analyzing device 100 in addition to the particle component measuring device 20. This also allows users of the particle component measuring device 20 to be informed of analysis information regarding a distance to the generation source.

The generation source analyzing device 100, the particle component measuring device 20, and the gas concentration measurement station 10 can be configured as a single apparatus. In this case, because the generation source analyzing device 100 has a particle component measuring function and a gas concentration measuring function, a measurement value can be acquired from a measuring section inside the apparatus without acquiring a measurement value of each concentration of a gas and a particle from another apparatus.

The acquiring section 110 may further acquire weather data as needed. For instance, the acquiring section 110 acquires weather data through a network from a weather DB 30 which is communicatively connected. The weather data may include data related to wind speed, wind direction, rainfall, temperature, and humidity and the like. The weather data acquired from the weather DB 30 may be stored in a memorizing section 130. The acquiring section 110 may acquire wind speed data in association with concentration measurement values of the gas and the particle component.

The analyzing section 120 analyzes a distance from a measurement point to the generation source 2 based on a concentration measurement value of the gas and a concentration measurement value of the particle component. Preferably, the analyzing section 120 may analyze a distance to the generation source 2 based on a concentration measurement value of a precursor gas and a concentration measurement value of a secondary generated particle component as described using FIG. 2 to FIG. 7.

The analyzing section 120 analyzes a distance to a generation source for each type of a plurality of precursor gases. For instance, a distance to a generation source of nitrogen oxides (NO$_X$) and a distance to a generation source of sulfur dioxides (SO$_2$) can be analyzed individually. The analyzing section 120 may have a correcting section 140. The correcting section 140 corrects an analysis result regarding a distance to the generation source 2 based on the weather data. However, the analyzing section 120 may not have the correcting section 140 depending on a required accuracy of an analysis result. For instance, when only knowing an outline of whether the distance to the generation source 2 is in a wide area or not is enough, the correcting section 140 is not necessarily needed, and the correcting section 140 may be omitted.

The correcting section 140 may have a reference distance setting section 142. The reference distance setting section 142 sets a reference distance, a first reference distance, and a second reference distance shown in FIG. 2 longer when a wind speed value in association with the concentration measurement value is larger. The correcting section 140 may have a delay time setting section 144. The delay time setting section 144 sets a delay time d of a second time range with respect to a first time range shown in FIG. 7, depending on wind speed data in association with a concentration measurement value. The correcting section 140 may correct not only the above reference distance and the like and the delay time, but may also correct the analysis result based on the weather data.

The analyzing section 120 may have an equilibrium state concentration calculating section 122 and a correlation value calculating section 124. The equilibrium state concentration calculating section 122 calculates an equilibrium state concentration of a secondary particle component which is generatable from the precursor gas, based on a measurement value of a precursor gas concentration 12. However, when the analyzing section 120 does not execute an analysis based on an equilibrium state concentration, the equilibrium state concentration calculating section 122 can be omitted. In the specification, 'an equilibrium state concentration of a secondary particle component' means a concentration of a secondary generated particle component which is generatable from the precursor gas when a reversible reaction of the precursor gas and the secondary generated particle component is in an equilibrium state.

The correlation value calculating section 124 calculates a correlation value between time-series data of measurement values of the precursor gas concentration 12 and time-series data of measurement values of a secondary generated particle component concentration 22. The correlation value may be a correlation coefficient r. The correlation coefficient r is calculate by Equation (1).

[Equation 1]

$$r = \frac{\sum_{i=1}^{n}(x_i - \bar{x})(y_i - \bar{y})}{\left(\left(\sum_{i=1}^{n}(x_i - \bar{x})^2\right)\left(\sum_{i=1}^{n}(y_i - \bar{y})^2\right)\right)^{\frac{1}{2}}} \quad (1)$$

$x_i$: A CONCENTRATION OF A TARGET SECONDARY GENERATED PARTICLE COMPONENT AT TIME i $\bar{x}$: ARITHMETIC MEAN OF A CONCENTRATION OF A TARGET SECONDARY GENERATED PARTICLE COMPONENT
$y_i$: A CONCENTRATION OF A TARGET PRECURSOR GAS AT TIME i
$\bar{y}$: ARITHMETIC MEAN OF A CONCENTRATION OF A TARGET PRECURSOR GAS The correlation value calculating section 124 calculates a correlation coefficient with respect to data for a predetermined time range (time window). The correlation value calculating section 124 calculates variation over time of the correlation coefficient by temporally shifting the time range. If weighting of data is equal, a center time of the time range may be deemed as a representative time of the calculated correlation coefficient. An arithmetic mean of Equation (1) is calculated for data within the above time range.

Because a concentration variation is generated due to solar radiation and change of atmospheric temperature, the time range may be as about one day. However, an average speed of conversion from the precursor gas to the particle depends also on the particle component as mentioned above. Therefore, the time range may be determined while taking an average speed of conversion into account.

The analyzing section 120 may have a separating section 150 and a direction analyzing section 160. The separating section 150 respectively separates time-series data of a concentration measurement value of a gas and time-series data of a concentration measurement value of the particle component into a first frequency band component and a second frequency band component. The analyzing section 120 may analyze a distance to a first generation source based on a correlation value between a first frequency band component regarding a concentration measurement value of a gas and a first frequency band component regarding a concentration measurement value of the particle component.

Similarly, the analyzing section 120 may analyze a distance to a second generation source based on a correlation value between a second frequency band component regarding a concentration measurement value of a gas and a second frequency band component regarding a concentration measurement value of the particle component. The direction analyzing section 160 may analyze a direction from the measurement point to the generation source 2 of the target component based on a gas concentration measurement value, a particle component concentration measurement value, and wind direction data. However, when the time-series data is not separated into a frequency band component and analyzed, the separating section 150 can be omitted. Also, when the direction to the generation source 2 is not analyzed, the direction analyzing section 160 can be omitted.

Figure 9:
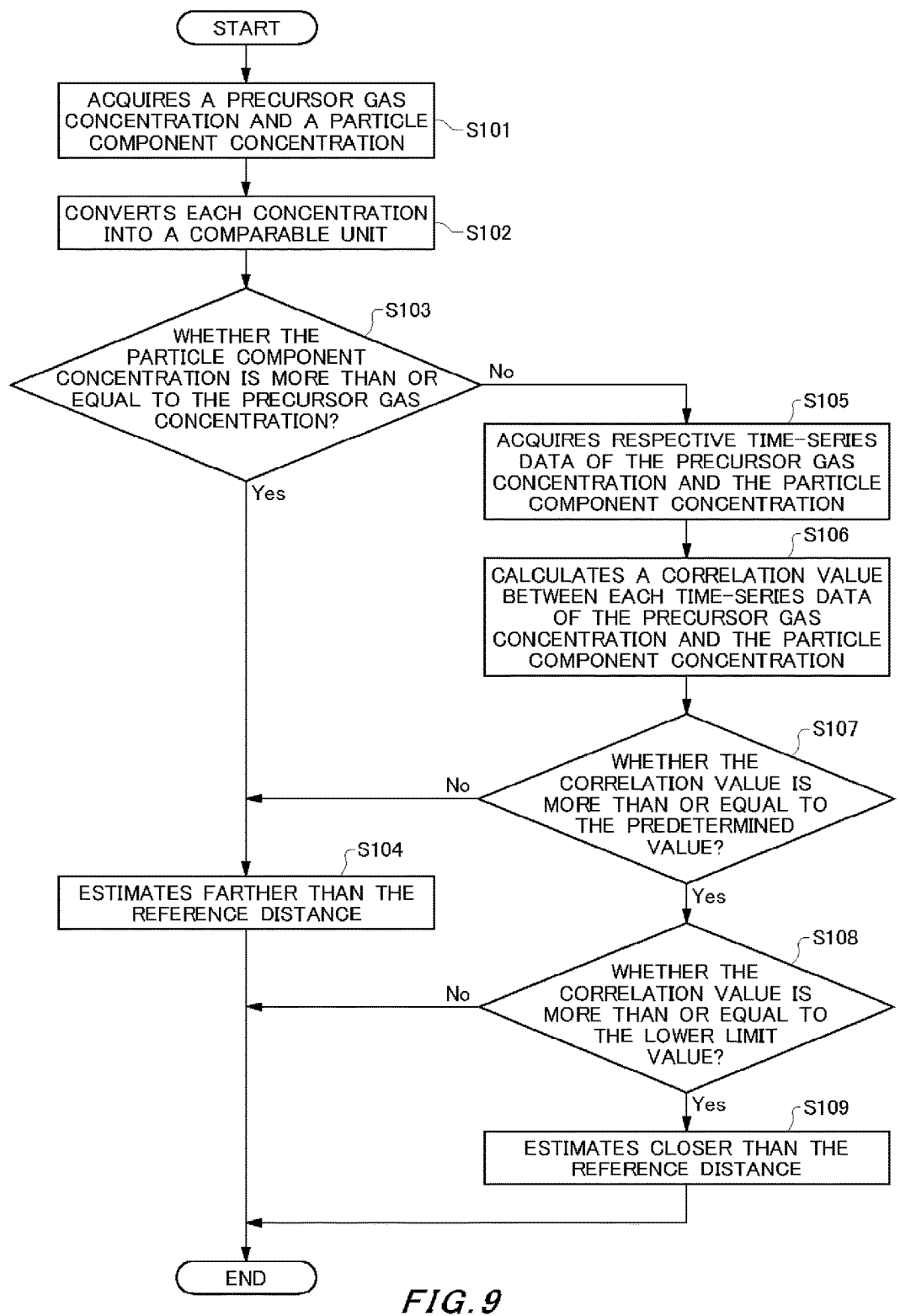
FIG. 9 is a flow chart showing a first example of an analyzing process by a generation source analyzing device 100.

FIG. 9 is a flow chart showing a first example of an analyzing process by a generation source analyzing device 100. The acquiring section 110 acquires a precursor gas concentration 12 and a particle component concentration (Step S101). The process of Step S101 corresponds to a step for acquiring a measurement value of a gas concentration and a measurement value of a particle component concentration which is generated in association with the gas. The particle component concentration may be a secondary generated particle component concentration 22. The precursor gas concentration 12 and the secondary generated particle component concentration 22 may be time-series data which have time resolution within an hour. However, in the process in Step S101, the precursor gas concentration 12 and the secondary generated particle component concentration 22 may not be necessarily time-series data, they may be concentration measurement values of one point or concentration measurement values of a plurality of points.

In the present example, the analyzing section 120 converts the precursor gas concentration 12 and the secondary generated particle component concentration 22 into comparable units (Step S102). The precursor gas concentration 12 is normally expressed by a volume concentration (ppb and the like), and the secondary generated particle component concentration 22 is normally expressed by a mass concentration ($\mu g/m^3$ and the like). The analyzing section 120 may convert respective units into molar concentration.

The analyzing section 120 compares a measurement value of the secondary generated particle component concentration 22 with a measurement value of the precursor gas concentration 12 (Step S103). If the secondary generated particle component concentration 22 is larger than or equal to the precursor gas concentration 12 (Step S103:YES), the analyzing section 120 estimates the distance from the measurement point to the generation source 2 is farther than the reference distance (Step S104). Therefore, the analyzing section 120 can determine the generation source 2 is positioned in a relatively wide area.

If the secondary generated particle component concentration 22 is below the precursor gas concentration 12 (Step S103: NO), the process proceeds to an analyzing process using a correlation value of Step S105 and subsequent steps. The acquiring section 110 acquires respective time-series data of the precursor gas concentration 12 and time-series data of the concentration of the particle component. In Step S101, if the time-series data is already acquired, the process of Step S105 is omitted. The correlation value calculating section 124 calculates a correlation value between time-series data of the concentration measurement values of the gas and time-series data of the concentration measurement values of the particle component (Step S106).

The analyzing section 120 determines whether the calculated correlation value is larger than or equal to the predetermined value (Step S107). If the calculated correlation value is below the predetermined value (Step S107: NO), it is determined that there is no correlation. Therefore, the analyzing section 120 estimates the distance from the measurement point to the generation source 2 is farther than the reference distance (Step S104). On the other hand, if the calculated correlation value is larger than or equal to the predetermined value (Step S107: YES), and if the measurement value of the secondary generated particle concentration of the target or the measurement value of the precursor gas concentration 12 is larger than or equal to a detection lower limit (Step S108: YES), the analyzing section 120 estimates the distance from the measurement point to the generation source 2 is closer than the reference distance (Step S109).

If the measurement value of the secondary generated particle concentration and the measurement value of the precursor gas concentration 12 is below the detection lower limit (Step S108: NO), the correlation value is apparently large. Therefore, the process may be finished without analyzing the distance to the generation source 2. In this case, because the secondary generated particle concentration itself is low, there is no need to analyze the generation source 2. Note that the predetermined value which is a reference to compare the correlation value may be set in advance. In general, if the correlation value is larger than or equal to 0, and smaller than or equal to 0.2, it is determined there is little correlation, and if the correlation value is larger than or equal to 0.4, it is determined there is considerably positive correlation. Therefore, the predetermined values may be set in a range larger than or equal to 0.1, and smaller than or equal to 0.4. The above mentioned processes from Step S102 to Step S109 correspond to one example of steps for analyzing the distance from the measurement point to the generation source 2 of the target component based on the concentration measurement value of the gas and the concentration measurement value of the particle component.

Because the analyzing process by the generation source analyzing device 100 of the present example analyzes the distance based on a measurement value of a concentration of a gas and a measurement value of a secondary generated particle concentration, differently from an analyzing method by an simulation model, so an analysis which reflects the actual situations is possible. Furthermore, an analysis of the generation source 2 of the secondary generated particle which is granulated in the atmosphere by a chemical reaction is possible. The analyzing process of the present example can distinguish whether the secondary particle component observed at the measurement point is due to the generation source near the measurement point, or is due to the generation source 2 relatively far from the measurement point. Therefore, it can be determined whether the secondary particle component is due to a local generation source 2 which municipalities should take measures, or is due to an wide-area generation source 2 which should be taken measures at a national level, the analyzing process of the present example can contribute to an effective generation source measure.

The analyzing process by the generation source analyzing device 100 of the present example jointly uses an analysis based on a correlation value between time-series data of a concentration measurement value of a gas and time-series data of a concentration measurement value of a particle component. Therefore, except when no precursor gas is observed and only a particle is observed, the analysis can be performed appropriately.

Figure 10:
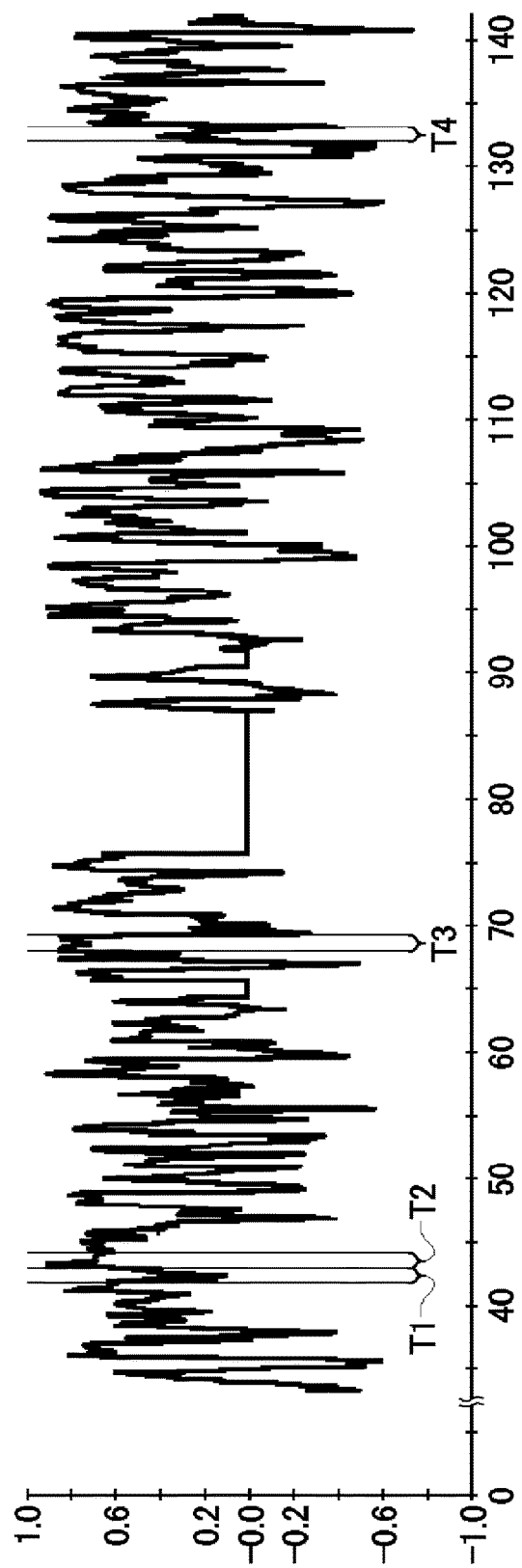
FIG. 10 is a diagram showing one example of a variation over time of a correlation value between a precursor gas concentration 12 and a secondary generated particle concentration.

FIG. 10 is a diagram showing one example of a variation over time of a correlation value between a precursor gas concentration 12 and a secondary generated particle concentration. In FIG. 10, a correlation value which is obtained with a first time range and a second time range as one day (24 hours) based on time-series data observed in an actual measurement point is shown. The correlation value between a concentration of sulfate acid ions which are negative ions in ammonium sulfates and a concentration of sulfur dioxides ($SO_2$) is calculated.

Among terms shown in FIG. 10, a term T1 and a term T4 in which correlation values show relatively small values, and a term T2 and a term T4 in which correlation values show larger values compared to T1 and T4 are selected, and are compared to a result of a simulation of a movement of air mass by a weather model. The comparison result is shown in the following Table 1 to Table 4. The HYSPLIT4 (HYbrid Single-Particle Lagrangian Integrated Trajectory) of National Oceanic and Atmospheric Administration (NOAA) is used as the weather model. The HYSPLIT is a model which can compute from where the air mass in a certain time and a certain point has moved (backward trajectory), and to where the air mass has moved (forward trajectory) based on weather data in all the countries of the world.

TABLE 1

| Term T1 | | |
|---|---|---|
| backward trajectory moving distance (24 hours) | number(s) | percentage |
| distance <200 km | 2 | 7% |
| 200 km ≤ distance <400 km | 9 | 32% |
| 400 km ≤ distance <800 km | 17 | 61% |

TABLE 2

| Term T4 | | |
|---|---|---|
| backward trajectory moving distance (24 hours) | number(s) | percentage |
| distance <200 km | 0 | 0% |
| 200 km ≤ distance <400 km | 3 | 11% |
| 400 km ≤ distance <800 km | 6 | 21% |
| distance ≥800 km | 19 | 68% |

In the cases of the term T1 and the term T4 in which correlation values show relatively small values, percentages of air mass which flies from a range with the distance below two hundred kilometers are respectively 7% and 0%. On the other hand, percentages of air mass which flies from larger than or equal to two hundred kilometers far are 93% and 100%.

TABLE 3

| Term T2 | | |
|---|---|---|
| backward trajectory moving distance (24 hours) | number(s) | percentage |
| distance <200 km | 30 | 68% |
| 200 km ≤ distance <400 km | 14 | 32% |
| 400 km ≤ distance <800 km | 0 | 0% |

TABLE 4

| Term T3 | | |
|---|---|---|
| backward trajectory moving distance (24 hours) | number(s) | percentage |
| distance <200 km | 14 | 47% |
| 200 km ≤ distance <400 km | 10 | 33% |
| 400 km ≤ distance <800 km | 0 | 20% |

On the other hand, in the cases of the term T2 and the term T3 in which correlation values show relatively larger values compared to the term T1 and the term T4, percentages of air mass which flies from a range with the distance below two hundred kilometers are respectively 68% and 47%. On the other hand, percentages of air mass which flies from larger than or equal to two hundred kilometers far are 32% and 53%.

From the results of the above, it can be understood that there are much air mass which flies from far in the term in which the correlation value is low compared to the term in which the correlation value is high. In this case, it can be said that the particle flies from the generation source 2 which is relatively far. In contrast, it can be understood that there are much air mass which flies from relatively near in the term in which the correlation coefficient is large. In this case, it can be said that the particle flies from the generation source 2 which is relatively near. Therefore, according to the analyzing process by the generation source analyzing device 100 of the present example, by the analyzing method with little calculation load, the analysis result similar to that by the large-scale simulation can be led.

Figure 11:
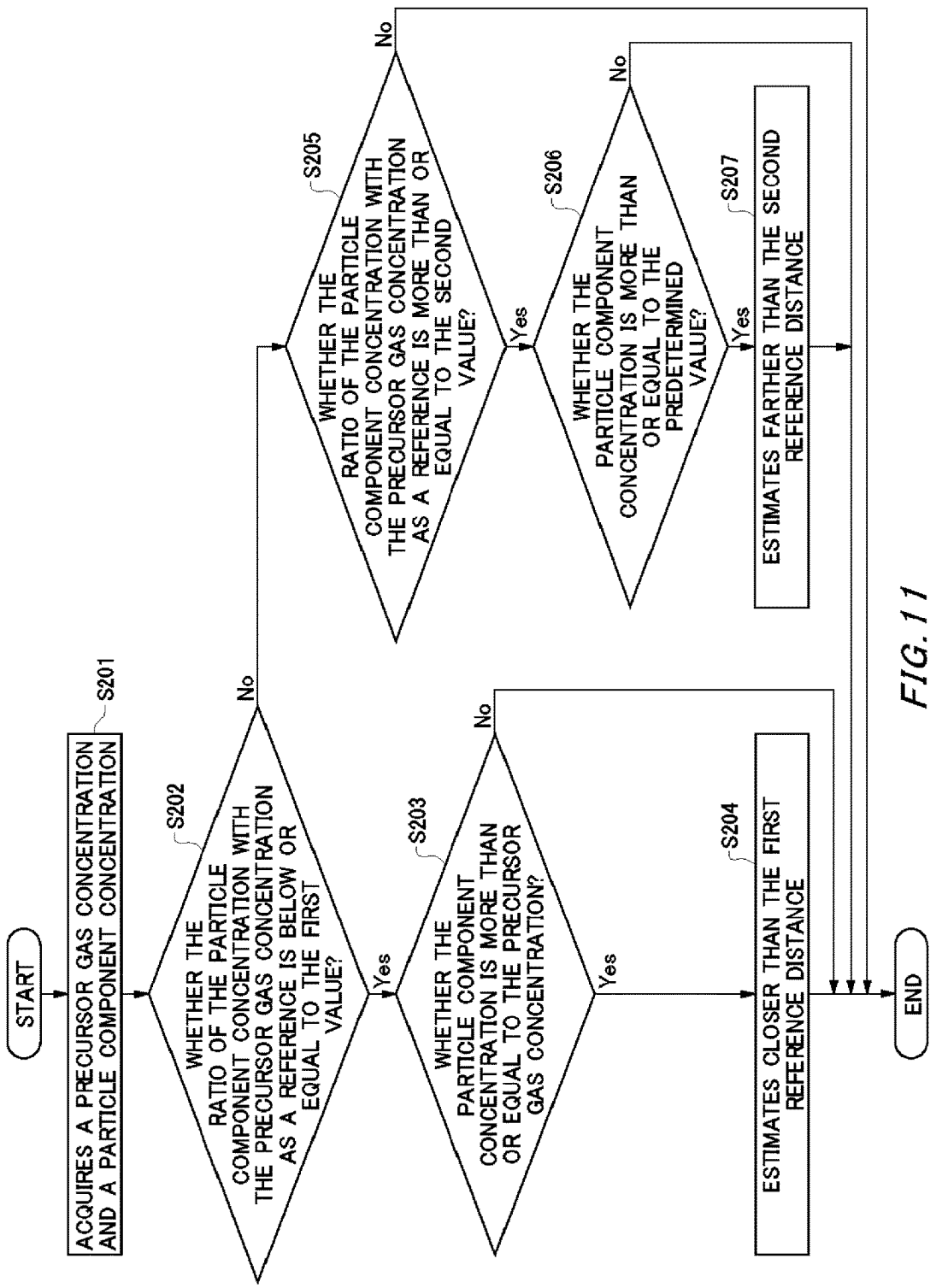
FIG. 11 is a flow chart showing a second example of an analyzing process by a generation source analyzing device 100.

FIG. 11 is a flow chart showing a second example of an analyzing process by a generation source analyzing device 100. The process of Step S201 is the same as the process of Step S101 in FIG. 9. The analyzing section 120 calculates a ratio of a secondary generated particle component concentration 22 with the precursor gas concentration 12 as a reference, and estimates a distance to the generation source 2 based on the ratio.

Specifically, the analyzing section 120 compares the ratio with a first value, if the ratio is smaller than or equal to the first value (Step S202: YES), and the precursor gas concentration 12 is larger than or equal to the predetermined value (Step S203: YES), the analyzing section 120 estimates the distance from the measurement point to the generation source 2 is closer than a first reference distance (Step S204).

If the measurement value of the secondary generated particle component concentration 22 and the measurement value of the precursor gas concentration 12 is below the detection lower limit, due to a noise and the like, apparently, the ratio of the secondary generated particle component concentration 22 with the precursor gas concentration 12 as a reference is sometimes calculated to be low. Therefore, even if the ratio is smaller than or equal to the first value (Step S202: YES), if the precursor gas concentration 12 is below the predetermined value (Step S203: NO), the process may be finished without analyzing the distance of the generation source 2.

If the calculated ratio is larger than the first value (Step S202: NO), the analyzing section 120 compares the calculated ratio with a second value (Step S205). The second value is set larger than the first value. If the ratio is larger than or equal to the second value (Step S205: YES), and if the secondary generated particle component concentration 22 is larger than or equal to the predetermined value (Step S206: YES), the analyzing section 120 estimates the distance from the measurement point to the generation source 2 is closer than a second reference distance (Step S204). The second reference distance is set longer than the first reference distance.

The first value and the second value may be set by an experiment or a simulation in advance, and stored in the memorizing section 130. According to the present example, in place of using a magnitude comparison or a difference of the concentration measurement value of the precursor gas and the concentration measurement value of the particle component in the first example, by using a ratio of a concentration measurement value of the precursor gas and a concentration measurement value of the particle component, the distance to the generation source 2 can be analyzed. Therefore, the step for converting the precursor gas concentration 12 and the secondary generated particle component concentration 22 into comparable units (Step S102 in FIG. 9) may be omitted.

Figure 12:
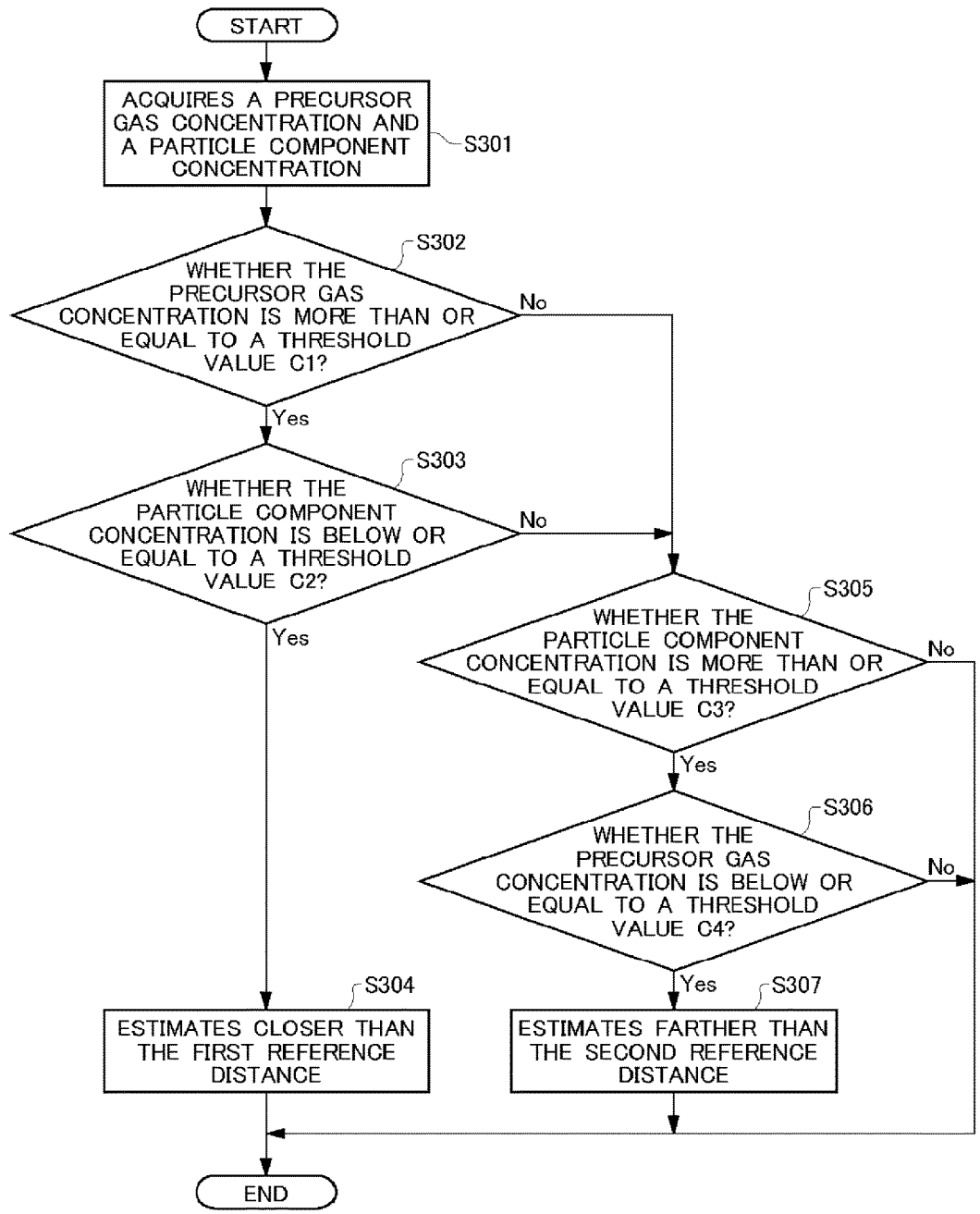
FIG. 12 is a flow chart showing a third example of an analyzing process by a generation source analyzing device 100.

FIG. 12 is a flow chart showing a third example of an analyzing process by a generation source analyzing device 100. Because the process of Step S301 is the same as the process of Step S101 in FIG. 9, a repetitive description will be omitted. In the present example, by comparing each of the precursor gas concentration 12 and the secondary generated particle component concentration 22 individually with threshold values $c_1$, $c_2$, $c_3$, $c_4$, the distance to the generation source 2 is analyzed.

If the measurement value of the precursor gas concentration 12 is larger than or equal to the predetermined threshold value $c_1$ (Step S302: YES), and the measurement value of the secondary generated particle component concentration 22 is smaller than or equal to the threshold value $c_2$ (Step S303: YES), the analyzing section 120 estimates the distance to at least one generation source 2 is closer than a first reference distance (Step S304). On the other hand, if the measurement value of the secondary generated particle component concentration 22 is larger than or equal to the predetermined threshold value $c_3$ (Step S305: YES), and the measurement value of the precursor gas concentration 12 is smaller than or equal to the threshold value $c_4$ (Step S306: YES), the analyzing section 120 estimates the distance to the generation source 2 which is position at the nearest is farther than a second reference distance (Step S307).

The threshold value $c_2$ may be set around zero. The threshold value $c_1$ and the threshold value $c_2$ are set so as to become '$c_1 > c_2$' when they are converted into comparable units. The threshold value $c_4$ may be set around zero. The threshold value $c_3$ and the threshold value $c_4$ can be set so as to become '$c_3 > c_4$', and so that $c_3$ becomes larger than or equal to a measurement lower limit value when they are converted into comparable units.

If even though the precursor gas concentration 12 is larger than or equal to the threshold value $c_1$ and if the precursor gas itself is observed (Step S302: YES), the secondary generated particle component concentration 22 is smaller than or equal to the threshold value $c_2$ and almost zero (Step S303: YES), it is thought that the precursor gas is diffused before the generated precursor gas changes into a secondary generated particle. Therefore, it can be estimated that the distance to the generation source 2 is closer than a first distance. On the other hand, if even though the secondary generated particle component concentration 22 is larger than or equal to the threshold value $c_3$ and the secondary generated particle itself is observed (Step S305: YES), if the precursor gas concentration 12 is smaller than or equal to the threshold value $c_4$ and almost zero (Step S306: YES), it can be estimated that the distance to the generation source 2 is farther than the reference distance.

As shown in FIG. 9, FIG. 11, and FIG. 12 of the above, in the specification, analyzing the distance from the measurement point to the generation source 2 of the target component based on the concentration measurement value of the precursor gas and the concentration measurement value of the particle component includes estimating the distance to the generation source 2 based on a magnitude comparison of the precursor gas concentration 12 and the secondary generated particle component concentration 22, a ratio of the precursor gas concentration 12 and the secondary generated particle component concentration 22, or a difference and the like.

Figure 13:
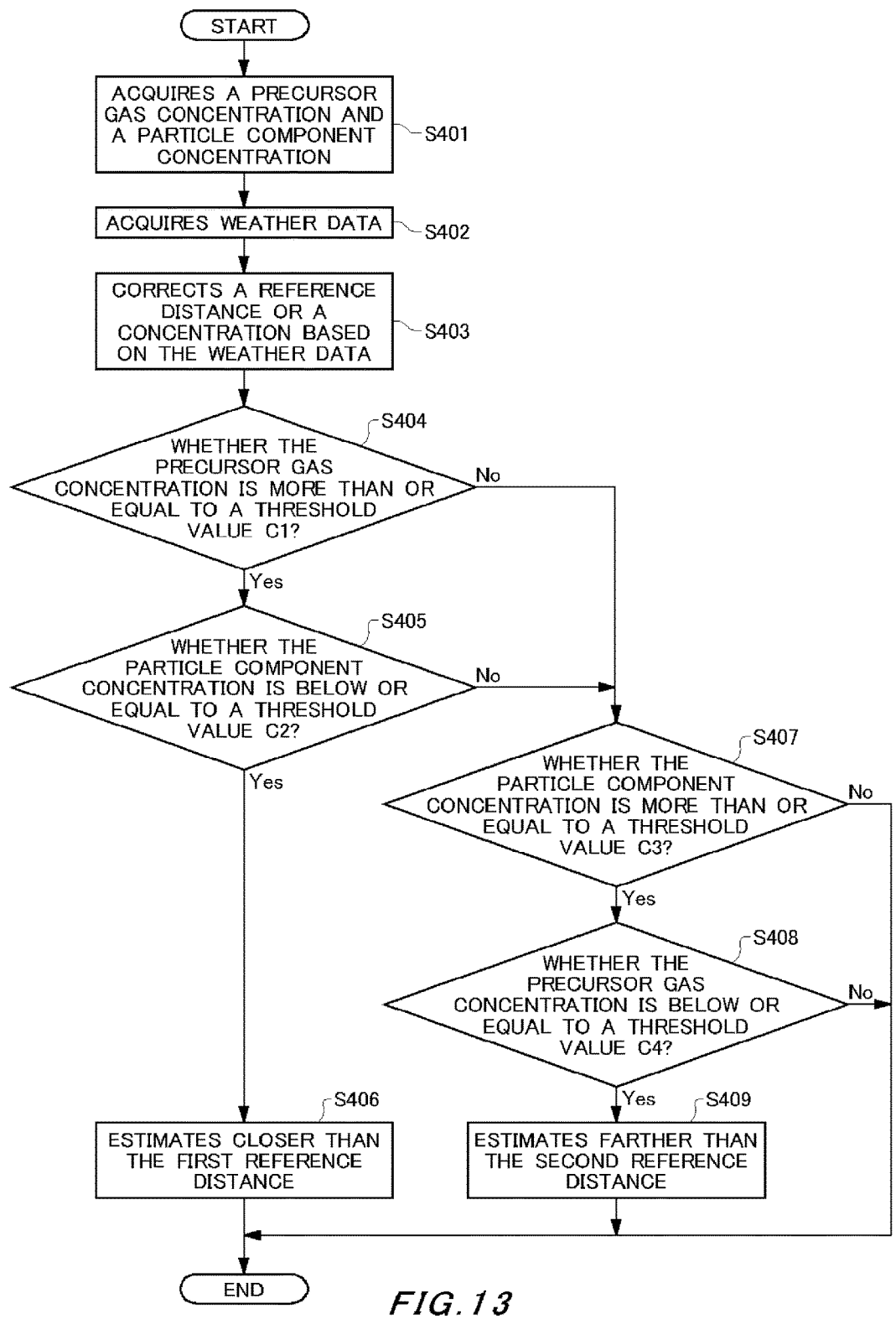
FIG. 13 is a flow chart showing a fourth example of an analyzing process by a generation source analyzing device 100.

FIG. 13 is a flow chart showing a fourth example of an analyzing process by a generation source analyzing device 100. The analyzing process of the present example is the same as the process of the third example in FIG. 12, except for the processes of Step S402 and Step S403. The processes of Step S401, and from Step S404 to Step S409 of the present example are the same as the processes from Step S301 to Step S307 in FIG. 12. Therefore, a repetitive description will be omitted.

The acquiring section 110 acquires weather data in association with a concentration measurement value of the gas and the particle component (Step S402). The weather data may include data related to wind speed, wind direction, rainfall, temperature, and humidity and the like. The acquiring section 110 may acquire weather data at a measurement point and a measurement time of the concentration of the gas and the particle component, as the weather data in association with the concentration measurement value. The weather data acquired from the weather DB 30 by the acquiring section 110 may be stored in a memorizing section 130.

The correcting section 140 corrects an analysis result regarding a distance to the generation source 2 based on the weather data. Specifically, the correcting section 140 may also correct an element related to a reference distance based on the weather data (Step S403). The correcting section 140 may also correct an element related to a concentration such as an actual measurement value of the precursor gas concentration 12 and an actual measurement value of the secondary generated particle component concentration 22 based on the weather data (Step S403).

For instance, the reaction of the precursor gas and the secondary generated particle is a chemical equilibrium reaction, and an equilibrium point changes depending on a temperature. Specifically, when the temperature is low, the precursor gas tends to become a particle, while when the temperature is high, it tends to be gasified. Therefore, because a tendency that the lower the atmospheric temperature becomes, the shorter the residence time of the precursor gas becomes is shown, the reference distance and the like may be corrected so as to become shorter. Also, the humidity affects a chemical reaction from sulfur dioxides to sulphuric acids. Because the less the water is, the less sulfide salts tend to be generated, the reference distance and the like may be corrected so as to become longer when the humidity becomes lower. Also, the temperature and the humidity affects a height which is reachable by the gas and the air which include a target component when the gas and the air are emitted. Because an average wind speed normal becomes larger when being apart from the earth's surface, the higher the reachable height is, the longer the diffusion range of the gas becomes.

The correcting section 140 may determine a reference wind speed in advance, correct a measurement value of the precursor gas concentration 12 and a measurement value of the secondary generated particle component concentration 22 based on the actual wind speed data, and calculate a reference concentration value assuming that it is reference wind speed. Then, the analyzing section 120 may take an influence of the wind speed into account by analyzing based on a reference concentration value of the precursor gas concentration 12 and a reference concentration value of the secondary generated particle component concentration 22 (from Step S404 to Step S409).

As above, regarding distance information such as a reference distance, delay time, and correction of a concentration, a correction amount or a calculation expression of a correction amount depending on weather data such as wind speed, temperature, humidity may be stored in the correction information DB 134 of the memorizing section 130 in advance. The correction amount or the calculation expression of the correction amount may be calculated using a simulation model in advance. The simulation model may be configured by appropriately combining local weather model, Euler type diffusion model, photochemical reaction model, secondary particle generation model, and deposition model and the like. In this case, if the correction amount and the calculation expression of the correction amount are once set, after that a simulation model in a corresponding-area or a global scale becomes unnecessary, which can prevent the scale of an analysis apparatus from becoming enormous.

However, the analyzing process of the present example is not limited to what stores a correction amount or a calculation expression of a correction amount in a memorizing section 130 in advance, the correcting section 140 may calculate the correction amount every time it analyzes. For instance, the correcting section 140 may also use a plume model which includes secondary particle generating process as an analysis type model, and calculate the correction amount. The plume model assumes that the diffusion in the state in which the wind is blowing becomes a normal distribution (Gaussian distribution), in addition, by giving a diffusion width, calculates change of a concentration due to the diffusion. The gas and the particle component are flowed by the wind in the atmosphere, while being diffused vertically and horizontally.

According to the present example, because an analysis result which includes an element related to a distance or a element related to a concentration can be corrected based on the weather data, an analysis result which reflects the actual situations can be obtained.

Figure 14:
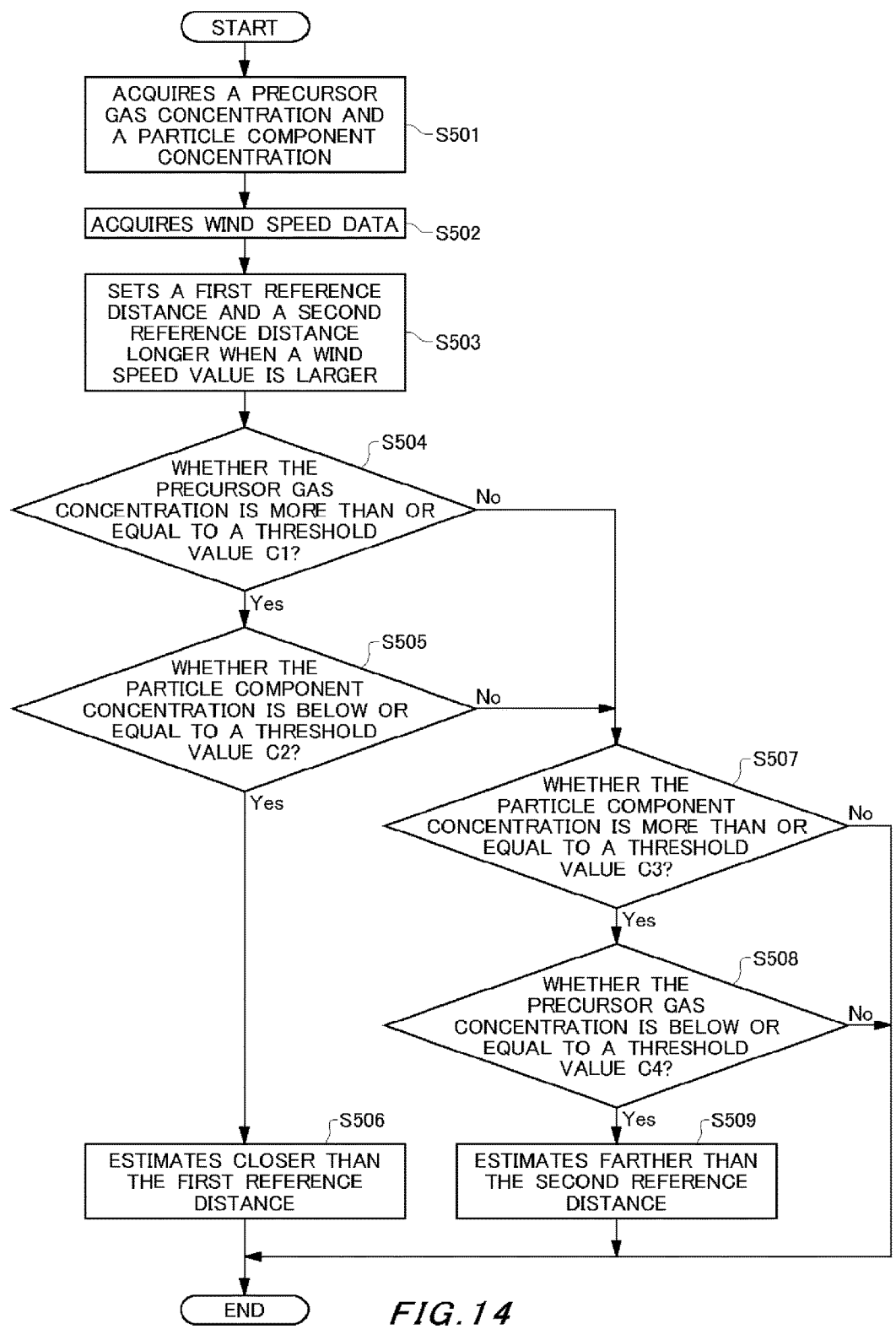
FIG. 14 is a flow chart showing a fifth example of an analyzing process by a generation source analyzing device 100.

FIG. 14 is a flow chart showing a fifth example of an analyzing process by a generation source analyzing device 100. The process shown in FIG. 14 is one example of a correction based on the weather data shown in FIG. 13. Step S501, and from Step S504 to Step S509 are the same as the processes in FIG. 12 and FIG. 13. Therefore, a repetitive description will be omitted.

The acquiring section 110 acquires wind speed data as one of the weather data in association with concentration measurement values of the gas and the particle component (Step S502). The acquiring section 110 may acquire wind speed data at a measurement point and a measurement time of the concentration of the gas and the particle component, as the wind speed data in association with the concentration measurement value. The acquiring section 110 may store the acquired wind speed data in the memorizing section 130.

The correcting section 140 corrects an analysis result regarding a distance to the generation source 2 based on the wind speed data. The diffusion range of the precursor gas depends on how much air mass (plume) is transported during the residence time. If the wind speed is large, the precursor gas is transported much farther. Therefore, the reference distance setting section 142 may set a reference distance, a first reference distance, and a second reference distance shown in FIG. 2 longer when a wind speed value in association with the concentration measurement value is larger. By correcting the element of the distance such as the first reference distance and the second reference distance depending on the wind speed, an analysis result conforming more to the actual circumstances can be obtained.

Figure 15:
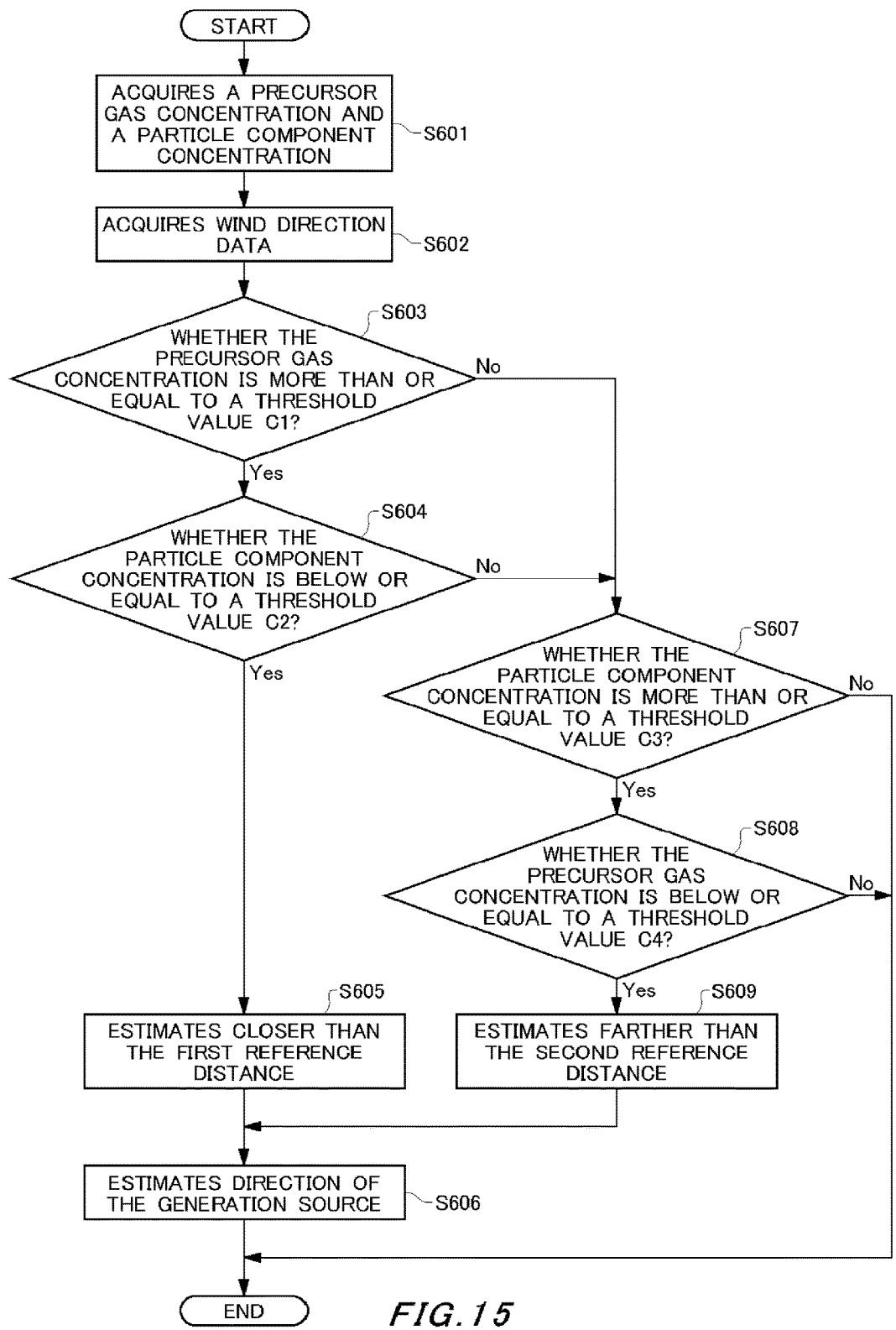
FIG. 15 is a flow chart showing a sixth example of an analyzing process by a generation source analyzing device 100.

FIG. 15 is a flow chart showing a sixth example of an analyzing process by a generation source analyzing device 100. The process shown in FIG. 15 is one example of a correction based on the weather data shown in FIG. 13. The processes of Step S601, from Step S603 to Step S605, and from Step S607 to Step S609 are the same as the processes in from FIG. 12 to FIG. 14. Therefore, a repetitive description will be omitted.

The acquiring section 110 acquires wind direction data as one of the weather data in association with concentration measurement values of the gas and the particle component (Step S602). The acquiring section 110 may acquire wind direction data at a measurement point and a measurement time of the concentration of the gas and the particle component, as the wind direction data in association with the concentration measurement value. The acquiring section 110 may also acquire the wind direction data while temporally going back over a predetermined time range with the measurement point of time as a reference.

The direction analyzing section 160 analyzes a direction from the measurement point to the generation source 2 of the target component based on a measurement value of the precursor gas concentration 12, a measurement value of the secondary generated particle component concentration 22, and the wind direction data. Specifically, the analyzing section 120 estimates the distance to the generation source 2 from the measurement value of the precursor gas concentration 12 and the measurement value of the secondary generated particle component concentration 22 (from Step S603 to Step S605, from Step S607 to Step S609). Then, the analyzing section 120 may calculate an average wind direction based on the wind direction data while temporally going back over the predetermined time range with the measurement point of time as a reference, and estimate the average wind direction is the direction of the generation source 2 (Step S606). The analyzing section 120 may also read map information from the map information DB 132, and display an estimated position range of the generation source 2 on the map information.

Figure 16:
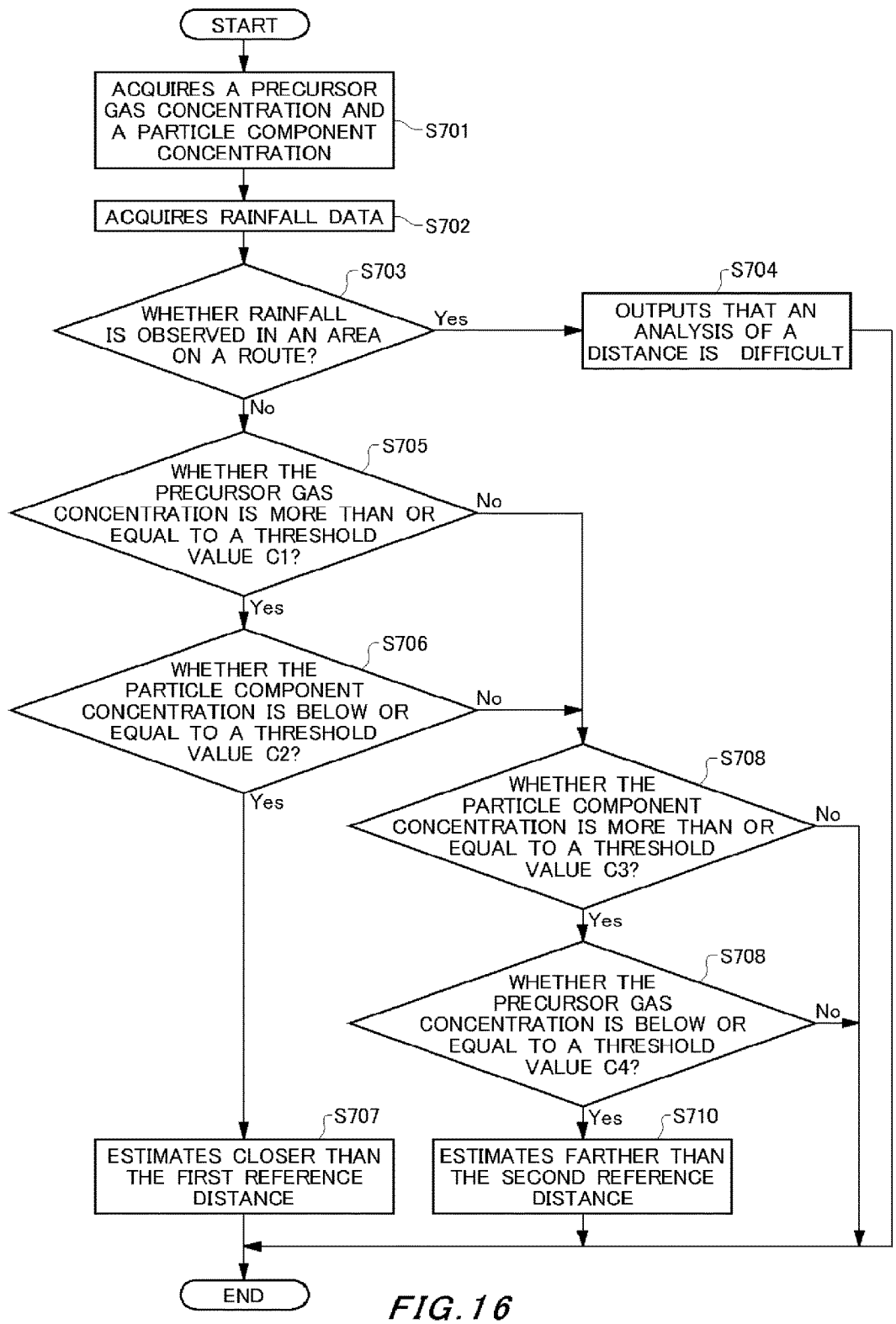
FIG. 16 is a flow chart showing a seventh example of an analyzing process by a generation source analyzing device 100.

FIG. 16 is a flow chart showing a seventh example of an analyzing process by a generation source analyzing device 100. The process shown in FIG. 16 is one example of a correction based on the weather data shown in FIG. 13. The processes of Step S701, and from Step S705 to Step S710 are the same as the processes in from FIG. 12 to FIG. 15. Therefore, a repetitive description will be omitted.

The acquiring section 110 acquires rainfall data as one of the weather data in association with concentration measurement values of the gas and the particle component (Step S702). The acquiring section 110 may acquire rainfall data at a measurement point and a measurement time of the concentration of the gas and the particle component, as the rainfall data in association with the concentration measurement value. The analyzing section 120 determines whether rainfall is observed in an area on a route from the measurement point to the generation source or not (Step S703). In the specification, the rainfall includes snowfall. The analyzing section 120 selects, for instance, an area of a predetermined width on a windward side based on the wind direction data as the area on the route from the measurement point to the generation source. For instance, the analyzing section 120 maps the area on the route and an area of rain clouds in a weather data on the map information read from the map information DB 132.

When rainfall is observed in an area on a route from the measurement point to the generation source 2 (Step S703: YES), the analyzing section 120 outputs that an analysis of a distance to the generation source 2 is difficult (Step S704). For instance, as a result of mapping of the above, when the overlapping state of the area on the route and the area on the rain clouds is larger than or equal to the predetermined value, the analyzing section 120 determines rainfall has been observed in the area on the route. When the rainfall is observed, a particle and a precursor gas in the air dissolve into the water, and are removed from the air. As a result, correlation between the precursor gas concentration 12 and the secondary generated particle component concentration 22 is lost. According to the process of the present example, when the rainfall is observed, users are given information that the analysis is difficult and an attention can be called.

In the above mentioned analyzing processes in from the fourth example to the seventh example shown in FIG. 13 to FIG. 16, the case in which a correcting process based on the weather data is applied to the process of the third example shown in FIG. 12 is described as an example. However, these correcting processes may also be applied to the first example and the second example shown in FIG. 9 and FIG. 11.

Figure 17:
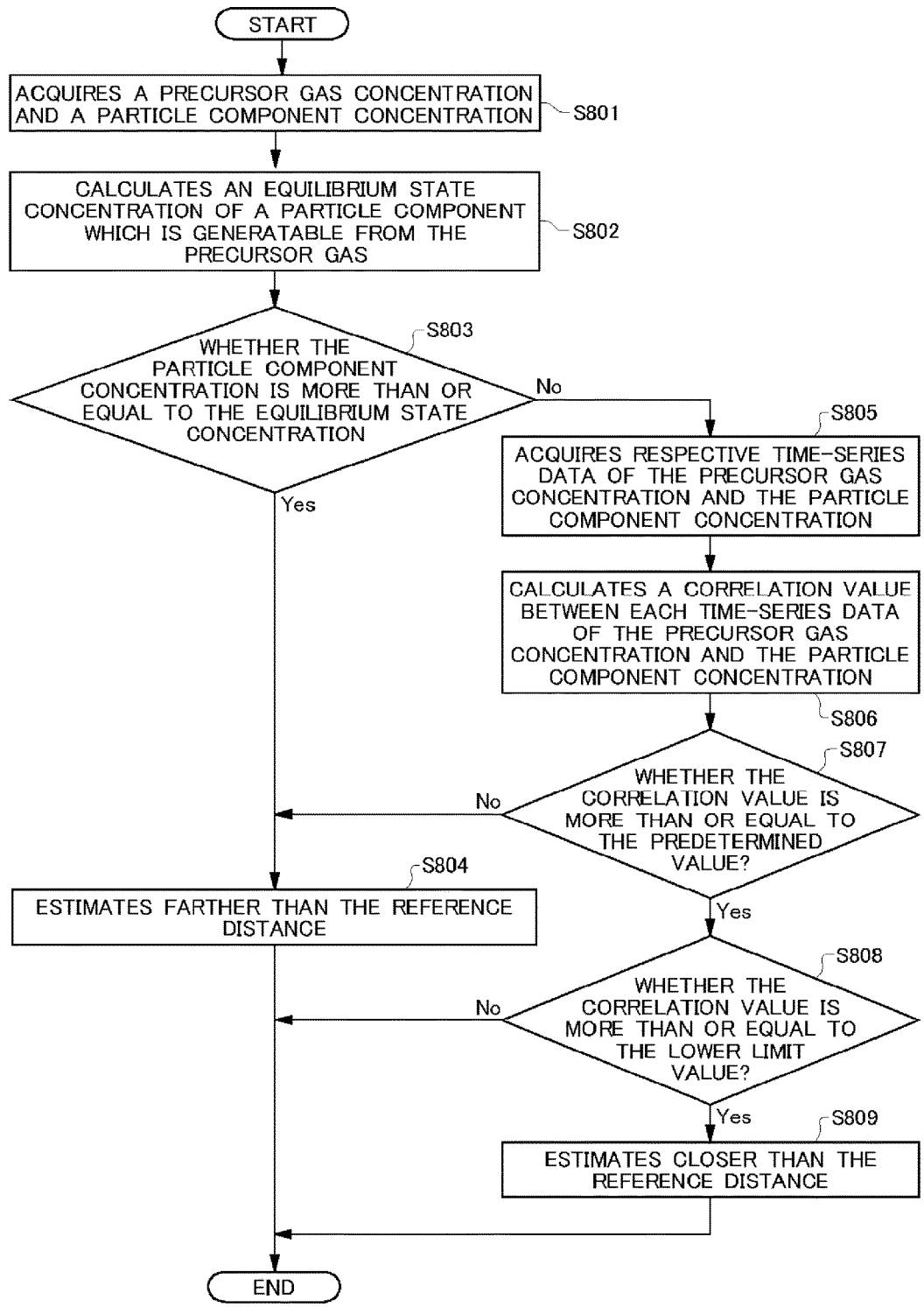
FIG. 17 is a flow chart showing an eighth example of an analyzing process by a generation source analyzing device 100.

FIG. 17 is a flow chart showing an eighth example of an analyzing process by a generation source analyzing device 100. The process shown in FIG. 17 is the same as the process of the first example shown in FIG. 9, except for the processes of Step S802 and Step S803.

The equilibrium state concentration calculating section 122 calculates an equilibrium state concentration of a secondary particle component which is generatable from the precursor gas, based on a measurement value of a precursor gas concentration 12 (Step S802). Specifically, the equilibrium state concentration calculating section 122 acquires temperature data from the weather DB 30. The equilibrium state concentration calculating section 122 calculates a secondary particle concentration which is generatable from the precursor gas as an equilibrium state concentration, based on a measurement value and a temperature of the precursor gas concentration 12, using a chemical equilibrium equation between the precursor gas and the secondary particle component. The equilibrium state concentration calculating section 122 may use an existing chemical reaction model such as CMB (Carbon Bond Mechanism, Version). The equilibrium state concentration calculating section 122 may convert a measurement value of the secondary particle concentration and a calculated value of the equilibrium state concentration into comparable units in the process of Step S802.

The analyzing section 120 analyzes a distance to the generation source 2 based on the calculated value of the equilibrium state concentration and the measurement value of the secondary generated particle component concentration 22.

The analyzing section 120 the present example compares a measurement value of the secondary generated particle component concentration 22 with a calculated value of the equilibrium state concentration (Step S803).

If the secondary generated particle component concentration 22 is larger than or equal to the precursor gas concentration 12 (Step S803:YES), the analyzing section 120 estimates the distance from the measurement point to the generation source 2 is farther than the reference distance (Step S804). Therefore, it is possible to determine the generation source 2 is positioned in a relatively wide area. According to the present example, because an analysis can be performed in consideration of an influence of the temperature in the process of calculate the equilibrium state concentration, an analysis conforming to the actual situations becomes possible.

In the present example, as one example for analyzing the distance to the generation source 2 based on a calculated value of the equilibrium state concentration and a measurement value of the secondary generated particle component concentration 22, a process which uses a calculated value of an equilibrium state concentration in place of the actual measurement value of the precursor gas concentration 12 in Step S103 in FIG. 9 is shown. However, the present example is not limited to this case. In the processes shown in FIG. 11 and FIG. 12, a calculated value of a equilibrium state concentration may also be used. Specifically, the analyzing section 120 may analyze a distance to the generation source 2 by a magnitude comparison, a difference, a ratio of the calculated value of the equilibrium state concentration and the concentration measurement value of the secondary generated particle component, and comparison with individual threshold values of respective values and the like.

Figure 18:
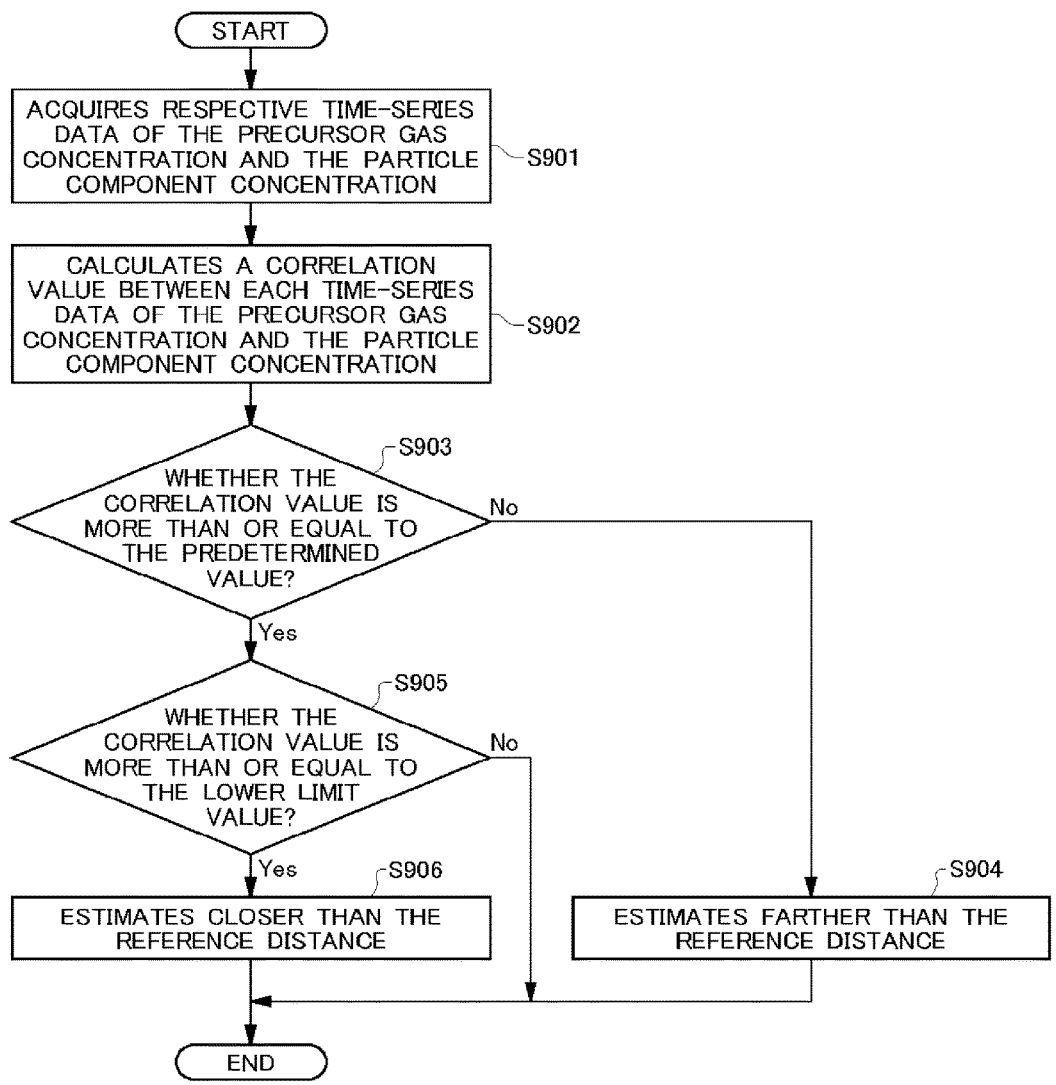
FIG. 18 is a flow chart showing a ninth example of an analyzing process by a generation source analyzing device 100.

FIG. 18 is a flow chart showing a ninth example of an analyzing process by a generation source analyzing device 100. In FIG. 9 and FIG. 17, an example in which an analyzing process is jointly used by the correlation value is shown, in addition to the process for comparing the precursor gas concentration 12 and the secondary generated particle component concentration 22. However, the process of analyzing a distance to the generation source 2 based on a correlation value between data of a first time range in time-series data of a concentration measurement value of a precursor gas and a data of a second time range in time-series data of a concentration measurement value of the secondary generated particle component may also be used singly. Because the specific process content is common as FIG. 9, a detailed description will be omitted.

Figure 19:
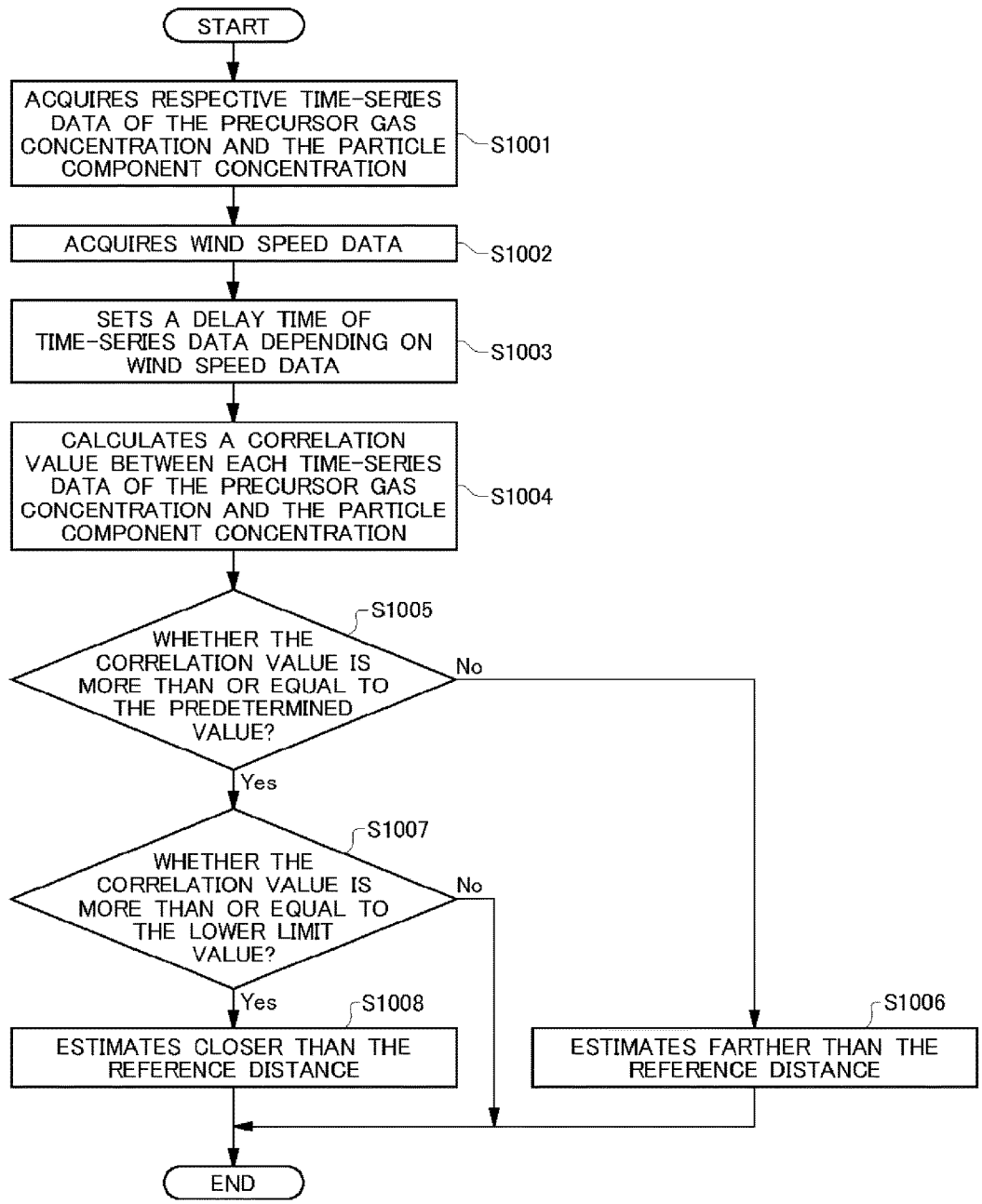
FIG. 19 is a flow chart showing a tenth example of an analyzing process by a generation source analyzing device 100.

FIG. 19 is a flow chart showing a tenth example of an analyzing process by a generation source analyzing device 100. The process shown in FIG. 19 is the same as the process in FIG. 18, except for the processes of Step S1002 and Step S1003. Specifically, the processes of Step S1001, and from Step S1004 to Step S1008 in FIG. 19 are the same as the processes from Step S901 to Step S906 in FIG. 18. Therefore, a repetitive description will be omitted.

The acquiring section 110 acquires wind speed data as one of the weather data in association with concentration measurement values of the gas and the particle component (Step S1002). The acquiring section 110 may acquire wind speed data at a measurement point and a measurement time of the concentration of the gas and the particle component, as the wind speed data in association with the concentration measurement value. The acquiring section 110 may store the acquired wind speed data in the memorizing section 130.

The delay time setting section 144 sets a delay time d of a second time range with respect to a first time range shown in FIG. 7, depending on wind speed data in association with a concentration measurement value. Because the diffusion state of the precursor gas and the particle component changes due to the wind speed data, the delay time d is also affected. A table which shows a relationship of the wind speed and a setting value of the delay time d or a calculation expression which calculates the setting value of the delay time d may be stored in the memorizing section 130 in advance.

Figure 20:
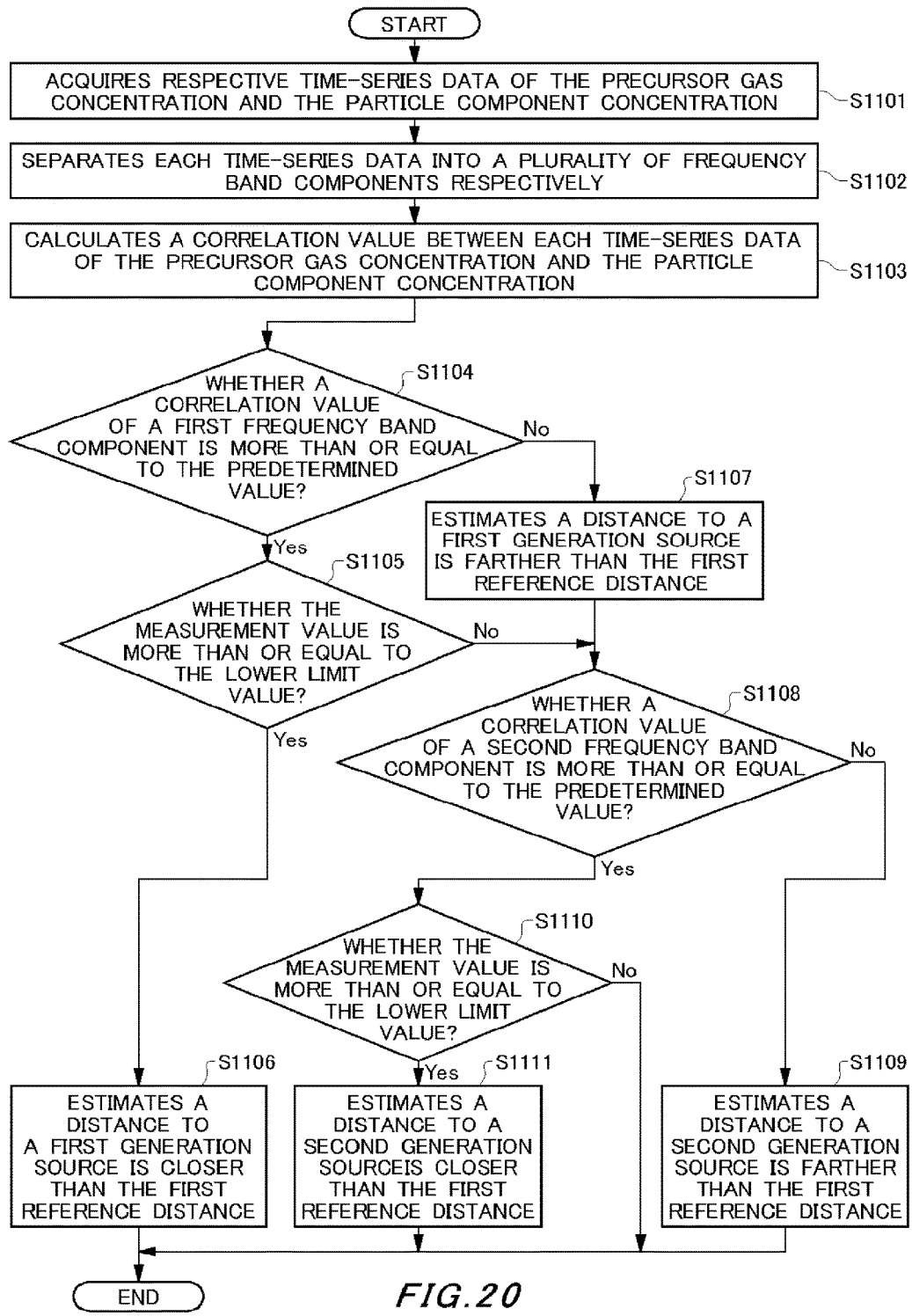
FIG. 20 is a flow chart showing an eleventh example of an analyzing process by a generation source analyzing device 100.

FIG. 20 is a flow chart showing an eleventh example of an analyzing process by a generation source analyzing device 100. The acquiring section 110 acquires a precursor gas concentration 12 and a particle component concentration (Step S1101). The separating section 150 respectively separates time-series data of the precursor gas concentration measurement value and time-series data of the concentration measurement value of the secondary generated particle component into a first frequency band component and a second frequency band component (Step S1102). The separating section 150, for instance, may make a frequency band component smaller than or equal to reference frequency $f_0$ as a first frequency band component, and a frequency band component higher than the reference frequency $f_0$ as a second frequency component. The reference frequency $f_0$ may be set in a range higher than a daily variation frequency (cycle 24 hours). For instance, the reference frequency $f_0$ is set in a range larger than or equal to 1 by 10 to the power of −5, and smaller than or equal to 1 by 10 to the power of −6. Time-series data of each concentration measurement value may also be separated into three or more frequency bands.

The correlation value calculating section 124 calculates a correlation value between a first frequency band component regarding a gas concentration measurement value and a first frequency band component regarding a secondary generated particle component concentration measurement value (Step S1103). Similarly, the correlation value calculating section 124 calculates a correlation value between a second frequency band component regarding a gas concentration measurement value and a second frequency band component regarding a secondary generated particle component concentration measurement value (Step S1103). Each correlation value may be a correlation coefficient.

The analyzing section 120 analyzes a distance to a first generation source related to a first frequency band component based on a correlation value between a first frequency band component regarding a gas concentration measurement value and a first frequency band component regarding a secondary generated particle component concentration measurement value. Specifically, the analyzing section 120 determines whether the calculated correlation value of a first frequency component is larger than or equal to the predetermined value (Step S1104). If the correlation value of the first frequency band component is larger than or equal to the predetermined value (Step S1104: YES), and if the measurement value of the secondary generated particle concentration of the target or the measurement value of the precursor gas concentration 12 is larger than or equal to a detection lower limit (Step S1105: YES), the analyzing section 120 estimates the distance from the measurement point to the first generation source related to the first frequency band component is closer than the reference distance (Step S1106).

On the other hand, if the calculated correlation value is below the predetermined value (Step S1104: NO), it is determined that there is no correlation. Therefore, the analyzing section 120 estimates the distance from the measurement point to the first generation source is farther than the reference distance (Step S1107). Then, the analyzing section 120 analyzes a distance to a second generation source related to a second frequency band component based on a correlation value between a second frequency band component regarding a gas concentration measurement value and a second frequency band component regarding a secondary generated particle component concentration measurement value.

Specifically, the analyzing section 120 determines whether the correlation value of a second frequency component is larger than or equal to the predetermined value (Step S1108). If the correlation value of the second frequency component is below the predetermined value (Step S1108: NO), the analyzing section 120 determines that there is no correlation. Therefore, the analyzing section 120 estimates the distance from the measurement point to the second generation source is farther than the reference distance (Step S1109).

If the correlation value of the second frequency component is larger than or equal to the predetermined value (Step S1108: YES), and if the measurement value of the secondary generated particle concentration of the target or the measurement value of the precursor gas concentration 12 is larger than or equal to a detection lower limit (Step S1110: YES), the analyzing section 120 estimates the distance from the measurement point to the second generation source related to the second frequency component is closer than the reference distance (Step S1111).

The process by the generation source analyzing device 100 of the present example can analyze a distance with respect to a plurality of generation sources with different time variation frequencies of emission amounts. The analysis can be made even if the first generation source is positioned in a wide area and the second generation source is positioned in a local area.

Figure 21:
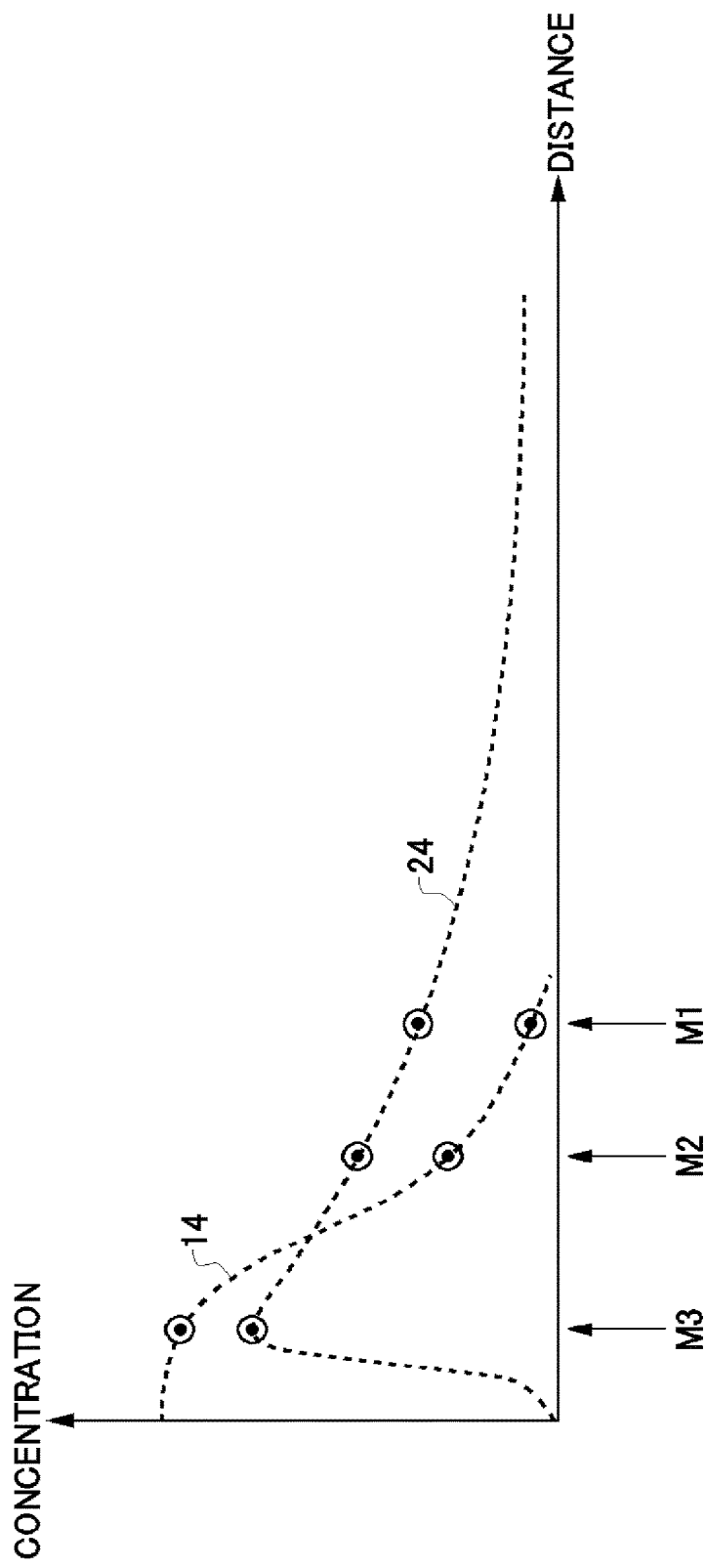
FIG. 21 is a diagram schematically showing an analysis of a distance to a generation source 2 based on concentration measurement values of a gas and a particle component at a plurality of measurement points.

FIG. 21 is a diagram schematically showing an analysis of a distance to a generation source 2 based on concentration measurement values of a gas and a particle component at a plurality of measurement points. In the present example, the acquiring section 110 acquires measurement values of the precursor gas concentration 12 at a plurality of measurement points and measurement values of the secondary generated particle component concentration 22 at a plurality of measurement points. The analyzing section 120 analyzes a distance to the generation source 2 based on concentration measurement values of the precursor gas at a plurality of measurement points and measurement values of the secondary generated particle component concentration 22 at a plurality of measurement points.

It is unknown to which point on the distance distribution curve the value at the measurement point M1 corresponds only from a concentration measurement value in one measurement point M1. In the present example, by acquiring concentration measurement values of the gas and the particle component in a plurality of points with different distance from the generation source 2 to each other, a distance distribution curve 14 of the precursor gas concentration 12 and a distance distribution curve 24 of the secondary generated particle component concentration 22 can be calculated.

The distance distribution curve 14 and the distance distribution curve 24 may be obtained using the Gaussian fitting technique for obtaining a function of an approximation curve (fitting curve) with respect to the Gaussian distribution. In FIG. 21, by applying the Gaussian fitting to precursor gas concentration measurement values at three measurement points M1, M2, and M3, the distance distribution curve 14 is calculated. Similarly, by applying the Gaussian fitting to secondary generated particle component measurement values at the measurement points M1, M2, and M3, the distance distribution curve 24 may be calculated.

If the position relationship of the measurement points M1, M2, and M3 is already known, by analyzing the calculated gradient of the distance distribution curve 14 of the precursor gas concentration 12 and the distance distribution curve 24 of the secondary generated particle component concentration 22, the position of the generation source 2 can be analyzed. For instance, in the position of the generation source 2, while taking into account that the distance distribution curve 14 of the precursor gas concentration 12 takes the maximum value, and the distance distribution curve 24 of the secondary generated particle component concentration 22 becomes around zero, the position of the generation source 2 is specified.

According to the present example, by calculating the distance distribution curve 14 of the precursor gas concentration 12 and the distance distribution curve 24 of the secondary generated particle component which are generated due to a difference of residence time of the precursor gas and the secondary generated particle component at a plurality of measurement points, and analyzing the gradient, the position of the generation source 2 can be narrowed.

Each embodiment in the specification can be combined appropriately. While the embodiments of the present invention have been described, the technical scope of the invention is not limited to the above described embodiments. It is apparent to persons skilled in the art that various alterations and improvements can be added to the above-described embodiments. It is also apparent from the scope of the claims that the embodiments added with such alterations or improvements can be included in the technical scope of the invention.

The operations, procedures, steps, and stages of each process performed by an apparatus, system, program, and method shown in the claims, embodiments, or diagrams can be performed in any order as long as the order is not indicated by "prior to," "before," or the like and as long as the output from a previous process is not used in a later process. Even if the process flow is described using phrases such as "first" or "next" in the claims, embodiments, or diagrams, it does not necessarily mean that the process must be performed in this order.

EXPLANATION OF REFERENCES

2: generation source,
10: gas concentration measurement station,
12: precursor gas concentration,
14: distance distribution curve,
20: particle component measuring device,
22: secondary generated particle component concentration,
24: distance distribution curve,
30: weather DB,
100: generation source analyzing device,
110: acquiring section,
120: analyzing section,
122: equilibrium state concentration calculating section,
124: correlation value calculating section,
130: memorizing section,
132: map information DB,
134: correction information DB,
140: correcting section,
142: reference distance setting section,
144: delay time setting section,
150: separating section,
160: direction analyzing section

What is claimed is:

1. A generation source analyzing device comprising:
   an acquiring section which acquires a concentration measurement value of a gas which includes a target component, and a concentration measurement value of a particle component which is generated in association with the gas, and
   an analyzing section configured to analyze a distance from a measurement point of the acquiring section to a generation source of the target component based on the concentration measurement value of the gas and the concentration measurement value of the particle component.

2. The generation source analyzing device according to claim 1, wherein
   the acquiring section acquires a concentration measurement value of a precursor gas which is a raw material to generate the particle component, and a concentration measurement value of a secondary generated particle component which is generated from the precursor gas.

3. The generation source analyzing device according to claim 2, wherein
   the analyzing section estimates the distance to at least one generation source is closer than a reference distance if the concentration measurement value of the precursor gas is higher than a predetermined value, and the concentration measurement value of the secondary generated particle component is lower than a first threshold value.

4. The generation source analyzing device according to claim 2, wherein
the analyzing section estimates the distance to a generation source which is positioned the nearest is farther than a reference distance if the concentration measurement value of the secondary generated particle component is higher than a predetermined value, and the concentration measurement value of the precursor gas is lower than a second threshold value.

5. The generation source analyzing device according to claim 3, wherein
the acquiring section acquires wind speed data in association with concentration measurement values of the precursor gas and the particle component, and
the analyzing section has a reference distance setting section which sets the reference distance longer when a wind speed value in association with the concentration measurement value is larger.

6. The generation source analyzing device according to claim 2, wherein
the analyzing section has a calculating section which calculates an equilibrium state concentration of the secondary generated particle component which is generatable from the precursor gas based on the concentration measurement value of the precursor gas, and
the analyzing section analyzes the distance to the generation source based on the calculated equilibrium state concentration and the concentration measurement value of the secondary generated particle component.

7. The generation source analyzing device according to claim 2, wherein
the acquiring section acquires the concentration measurement value for each type of a plural types of the precursor gases, and the concentration measurement values for each type of the secondary generated particle components which are generated from the respective precursor gases,
the analyzing section analyzes a distance to a generation source for each type of the precursor gases.

8. The generation source analyzing device according to claim 2, wherein
the acquiring section respectively acquires time-series data as concentration measurement values of a precursor gas and concentration measurement values of the particle component, and
the analyzing section analyzes the distance to the generation source based on a correlation value between time-series data of the concentration measurement values of the precursor gas and time-series data of the concentration measurement values of the particle component.

9. The generation source analyzing device according to claim 8, wherein
the analyzing section analyzes the distance to the generation source based on a correlation value between
data for a first time range in time-series data of the concentration measurement values of the precursor gas, and
data for a second time range which is more delayed than the first time range, in time-series data of the concentration measurement values of the particle component.

10. The generation source analyzing device according to claim 9, wherein
the acquiring section acquires wind speed data in association with concentration measurement values of the precursor gas and the particle component, and
the analyzing section has a delay time setting section which sets a delay time of the second time range with respect to the first time range depending on the wind speed data.

11. The generation source analyzing device according to claim 8, wherein
when at least one of the concentration measurement value of the particle component and the concentration measurement value of the precursor gas is larger than or equal to a predetermined lower limit value, and when the correlation value between time-series data of the concentration measurement value of the particle component and time-series data of the concentration measurement value of the precursor gas is higher than a predetermined reference, the analyzing section estimates the distance to at least the one generation source is closer than a predetermined reference distance.

12. The generation source analyzing device according to claim 8, wherein the analyzing section:
has a separating section which respectively separates time-series data of the concentration measurement value of the precursor gas and time-series data of the concentration measurement value of the particle component into a first frequency band component and a second frequency band component;
analyzes a distance to a first generation source based on a correlation value between the first frequency band component regarding the concentration measurement value of the precursor gas and the first frequency band component regarding the concentration measurement value of the particle component; and
analyzes a distance to a second generation source based on a correlation value between the second frequency band component regarding the concentration measurement value of the precursor gas and the second frequency band component regarding the concentration measurement value of the particle component.

13. The generation source analyzing device according to claim 1, wherein
the acquiring section further acquires weather data, and
the analyzing section corrects an analysis result regarding a distance to the generation source using the weather data.

14. The generation source analyzing device according to claim 13, wherein
the acquiring section acquires wind speed data as the weather data.

15. The generation source analyzing device according to claim 13, wherein
the acquiring section acquires wind direction data as the weather data, and
the analyzing section has a direction analyzing section which analyzes a direction from the measurement point to the generation source of the target component based on the concentration measurement value of the gas including the target component, the concentration measurement value of the particle component which is generated in association with the gas, and the wind direction data.

16. The generation source analyzing device according to claim 13, wherein
the acquiring section acquires rainfall data as the weather data, and
the analyzing section outputs that an analysis of the distance to the generation source is difficult when rainfall is observed in an area on a route from the measurement point to the generation source.

17. The generation source analyzing device according to claim 2, wherein
- the acquiring section acquires concentration measurement values of a precursor gas at a plurality of measurement points and concentration measurement values of the particle component at a plurality of measurement points, and
- the analyzing section analyzes the distance to the generation source based on the concentration measurement values of the precursor gas at a plurality of measurement points and the concentration measurement values of the particle component at a plurality of measurement points.

18. A generation source analyzing method comprising:
- acquiring a concentration measurement value of a gas which includes a target component and a concentration measurement value of a particle component which is generated in association with the gas; and
- analyzing a distance from a measurement point of an acquiring section to a generation source of the target component based on a concentration measurement value of the gas and a concentration measurement value of the particle component.

* * * * *